(12) United States Patent
Yoskowitz

(10) Patent No.: US 11,311,364 B2
(45) Date of Patent: Apr. 26, 2022

(54) HAND-HELD THERAPEUTIC ORAL DEVICE FOR COOLING ORAL TISSUE OF A USER

(71) Applicant: CHEMOMOUTHPIECE, LLC, Closter, NJ (US)

(72) Inventor: David Yoskowitz, Woodcliff Lake, NJ (US)

(73) Assignee: CHEMOMOUTHPIECE, LLC, Closter, NJ (US)

( * ) Notice: Subject to any disclaimer, the term of this patent is extended or adjusted under 35 U.S.C. 154(b) by 267 days.

(21) Appl. No.: 15/875,395

(22) Filed: Jan. 19, 2018

(65) Prior Publication Data
US 2018/0140407 A1 May 24, 2018

Related U.S. Application Data

(63) Continuation-in-part of application No. 15/687,969, filed on Aug. 28, 2017, which is a (Continued)

(51) Int. Cl.
*A61C 19/06* (2006.01)
*A61C 19/08* (2006.01)
(Continued)

(52) U.S. Cl.
CPC ............ *A61C 19/06* (2013.01); *A61C 1/0069* (2013.01); *A61C 19/08* (2013.01); *A61F 7/10* (2013.01);
(Continued)

(58) Field of Classification Search
CPC . A61C 19/06; A61C 19/08; A61F 2007/0017; A61F 2007/0287; A61F 7/12; A61J 17/02
See application file for complete search history.

(56) References Cited

U.S. PATENT DOCUMENTS 3,439,681 A    4/1969    Riley
3,467,104 A    9/1969    Burbridge
(Continued)

FOREIGN PATENT DOCUMENTS

CN            203089443 U    7/2013
EP    004558393-0001 S    1/2018
(Continued)

OTHER PUBLICATIONS

International Search Report and Written Opinion dated Jun. 8, 2017 for corresponding international patent application No. PCT/US2017/025870.
(Continued)

*Primary Examiner* — Kaitlyn E Smith
(74) *Attorney, Agent, or Firm* — Abelman, Frayne & Schwab

(57) ABSTRACT

The invention is directed to a mouth piece for cooling of oral tissue of a patient during chemotherapy treatment. The mouth piece includes a cooling medium contained within the top element and the bottom element and able to retain a cooling environment within the mouth sufficient to reduce capillary blood flow to the patient's mouth. In one embodiment, an external chamber extends from the front of the mouth piece to house a cooling medium. A bladder is positioned inside the external chamber for storing a solution having a freezing temperature above the freezing point temperature of the cooling medium to assist in cooling the cooling medium.

19 Claims, 34 Drawing Sheets

Related U.S. Application Data continuation-in-part of application No. PCT/US2017/025870, filed on Apr. 4, 2017.

(60) Provisional application No. 62/460,195, filed on Feb. 17, 2017, provisional application No. 62/317,786, filed on Apr. 4, 2016.

(51) Int. Cl.
*A61F 7/12* (2006.01)
*A61C 1/00* (2006.01)
*A61F 7/10* (2006.01)
*A61F 7/00* (2006.01)
*A61F 7/02* (2006.01)

(52) U.S. Cl.
CPC ............... *A61F 7/12* (2013.01); *A61F 7/123* (2013.01); *A61C 2203/00* (2013.01); *A61F 2007/0017* (2013.01); *A61F 2007/0056* (2013.01); *A61F 2007/0219* (2013.01); *A61F 2007/0287* (2013.01); *A61F 2007/101* (2013.01); *A61F 2007/108* (2013.01)

(56) References Cited

U.S. PATENT DOCUMENTS

| | | | |
|---|---|---|---|
| 3,875,940 | A | 4/1975 | Beuther |
| 4,983,122 | A | 1/1991 | Mitnick |
| 5,494,441 | A * | 2/1996 | Nicholson .......... A61C 17/0211 433/215 |
| 5,509,801 | A | 4/1996 | Nicholson |
| 5,527,351 | A | 6/1996 | Friedman |
| 5,636,379 | A | 6/1997 | Williams |
| 5,676,691 | A | 10/1997 | Friedman |
| 5,819,744 | A | 10/1998 | Stoyka, Jr. |
| 6,217,606 | B1 | 4/2001 | Portnoy et al. |
| 6,660,029 | B2 | 12/2003 | VanSkiver et al. |
| 6,811,338 | B1 * | 11/2004 | Manske, Jr. .......... A45D 40/00 401/7 |
| 7,044,929 | B2 | 5/2006 | VanSkiver et al. |
| 7,527,642 | B2 | 5/2009 | VanSkiver et al. |
| 7,934,687 | B2 | 5/2011 | Crook |
| 9,572,645 | B2 | 2/2017 | Levine |
| 9,644,880 | B2 * | 5/2017 | Paul .................. A61F 7/106 |
| 10,123,860 | B2 | 11/2018 | Levine |
| 2003/0055474 | A1 | 3/2003 | VanSkiver et al. |
| 2004/0106970 | A1 | 6/2004 | VanSkiver et al. |
| 2004/0158303 | A1 | 8/2004 | Lennox |
| 2004/0234456 | A1 | 11/2004 | Slaughter |
| 2004/0244412 | A1 * | 12/2004 | Trinh .................. A61F 7/103 62/530 |
| 2006/0161234 | A1 | 7/2006 | VanSkiver |
| 2009/0044731 | A1 | 2/2009 | Crook |
| 2009/0216303 | A1 | 8/2009 | VanSkiver et al. |
| 2009/0312823 | A1 | 12/2009 | Patience |
| 2011/0000022 | A1 | 1/2011 | Schlanger |
| 2013/0085530 | A1 | 4/2013 | Caputo |
| 2013/0138185 | A1 | 5/2013 | Paxman |
| 2013/0183635 | A1 | 7/2013 | Wilhoit |
| 2013/0245729 | A1 * | 9/2013 | Edelman .................. A61F 7/10 607/104 |
| 2014/0276254 | A1 | 9/2014 | Varga |
| 2014/0343641 | A1 | 11/2014 | Barbut |
| 2015/0016755 | A1 | 1/2015 | Sheikh |
| 2015/0037749 | A1 | 2/2015 | Levine |
| 2016/0278977 | A1 | 9/2016 | Pansmith |
| 2017/0020722 | A1 * | 1/2017 | Maher .................. A61F 5/055 |
| 2017/0143596 | A1 | 5/2017 | Levine |
| 2017/0197051 | A1 | 7/2017 | Kumpel |
| 2017/0224455 | A1 | 8/2017 | Levine |
| 2017/0231815 | A1 | 8/2017 | Berg et al. |
| 2017/0354535 | A1 | 12/2017 | Yoskowitz |
| 2018/0169504 | A1 * | 6/2018 | Williams ............. A63B 71/085 |

FOREIGN PATENT DOCUMENTS

| | | |
|---|---|---|
| EP | 004558393-0002 S | 1/2018 |
| JP | H114839 | 1/1999 |
| WO | 2013039906 A1 | 3/2013 |
| WO | 2016/023920 | 2/2016 |
| WO | 2017176697 A1 | 10/2017 |

OTHER PUBLICATIONS

Ohyama and Ebihara, "Pilot study of ice-ball cryotherapy for radiation-induced oral mucositis"; Gan No Rinsho; ISSN 0021-4949; Coden Ganrae; v. 42(2); 1996; p. 161-164; Japan.

Svanberg et al., "The effect of cryotherapy on oral mucosa: a study in healthy volunteers"; Medical Oncology Dec. 2012, vol. 29, Issue 5, pp. 3587-3591.

Keefe, Powerpoint slides for "Mucositis Management Guidelines: Update 2005", Multinational Association of Supportive Care in Cancer (MASCC/ISOO); 2005.

Lalla et al., "MASCC/ISOO Clinical Practice Guidelines for the Management of Mucositis Secondary to Cancer Therapy", Multinational Association of Supportive Care in Cancer (MASCC/ISOO); published online Feb. 25, 2014.

Kadakia et al., "Supportive Cryotherapy; A Review from Head to Toe", J Pain Symptom Manage; 47(6); pp. 1100-1115; Jun. 2014.

Riley et al., "Interventions for preventing oralmucositis in patients with cancer receiving treatment: oral cryotherapy (Review)", Cochrane Database of Systematic Reviews 2015, Issue 12. Art. No. CD011552.

Peterson et al., "Systematic review of oral cryotherapy for management of oral mucositis caused by cancer therapy", Springer-Verlag; published online Sep. 21, 2012.

Chaveli-Lopez et al., "Treatment of oral mucositis due to chemotherapy", J Clin Exp Dent. 8(2): e201-9; Jan. 8, 2016.

Walladbegi et al., "New Cooling Device for Oral Mucosa Better Tolerated and Equally Effective As Ice Cooling", Blood Journal, 2016; retrieved from the Internet at URL: http://www.bloodjournal.org/content/128/22/5806?sso-checked=true.

Homepage for Braincool website; retrieved from the Internet on Apr. 19, 2018 at URL: http://www.braincool.se/.

Mucositis—The Oral Cancer Foundation; retrieved from the Internet on Apr. 19, 2018 at URL: http://oralcancerfoundation.org/complications/mucositis/.

Malik, "Oral Mucositis in Cancer Patients: Treatment Update", Cancer Therapy Advisor; May 10, 2012; retrieved from the Internet at URL: http://www.cancertherapyadvisor.com/side-effect-management/oral-mucositis-in-cancer-patients-treatment-update/article/240497/.

"Ice Chips Prevent Mouth Sores Associated with High-Dose Chemotherapy", CancerConnect.com; retrieved from the Internet on Apr. 19, 2018 at URL: http://news.cancerconnect.com/ice-chips-prevent-mouth-sores-associated-with-high-dose-chemotherapy/.

"Using ice chips reduces oral mucositis in patients undergoing chemotherapy", National Elf Service; retrieved from the Internet on Apr. 19, 2018 at URL: https://www.nationalelfservice.net/dentistry/oral-medicine-and-pathology/using-ice-chips-reduces-oral-mucositis-in-patients-undergoing-chemotherapy/.

"How to Prevent Mouth Problems During Cancer Treatment", Dana-Farber Cancer Institute; published Jan. 17, 2014; retrieved from the Internet at URL: http://blog.dana-farber.org/insight/2014/01/how-to-prevent-mouth-problems-during-cancer-treatment/.

Jenkins, "A Cold, Hard Solution for Oral Mucositis", JAMA Oncol. Published online Sep. 1, 2016; retrieved from the Internet at URL: http://www.medscape.com/viewarticle/868718.

Singapore Application No. SG 11201808539W—Search Report and Written Opinion, dated Dec. 6, 2019.

International Search Report and Written Opinion for PCT/US2019/014237, dated May 15, 2019.

Indian patent Application No. IN 201847040926—First Examination Report (FER) under Sections 12 & 13 of the Patents Act; dated Jun. 16, 2021; 8 pages.

* cited by examiner

ND-HELD THERAPEUTIC ORAL DEVICE FOR COOLING ORAL TISSUE OF A USER

CROSS REFERENCE TO RELATED APPLICATIONS

This application is a continuation-in-part of U.S. application Ser. No. 15/687,969, filed Aug. 28, 2017, which is a continuation-in-part of PCT International Application No. PCT/US2017/025870, filed Apr. 4, 2017, which claims the benefit of U.S. Provisional Application No. 62/317,786, filed Apr. 4, 2016, and U.S. Provisional Application No. 62/460,195, filed Feb. 17, 2017, all of which are hereby incorporated by reference.

FIELD OF THE INVENTION

The present invention relates to a mouth piece for cooling of oral tissue of a patient during chemotherapy treatment.

BACKGROUND OF THE INVENTION

One of the most limiting side effects associated with chemotherapy treatments of cancer patients is the condition characterized by severe inflammation of the oral mucous membrane tissues known as mucositis. This inflammation produces oral sores that are so painful for the patient that frequently the chemotherapy treatments must be weakened or even discontinued before they are completed. As a result, cancer patients oftentimes can not be given the necessary amount of chemotherapy to effectively treat their conditions. As well, often new treatments undergoing investigator evaluation have patients who withdraw from the protocol because of a lack of tolerance of the mucositis often creating significant issues in evaluating the tests.

It has been known, however, that keeping the oral tissues cold during chemotherapy treatments causes vasoconstriction of the associated blood vessels which reduces the amount of chemotherapy agent flowing into this tissue. The known method of cooling the oral tissues comprises periodically placing ice within the patient's mouth during the administration of the chemotherapy agent. This method lessens the formation of oral sores for short treatment periods of less than about one hour.

Although the known method of cooling the oral tissues has been acceptable for short treatments, it is impractical for extended chemotherapy treatments that may continue for extended periods, for at least the following reasons. First, it is quite difficult for the patient to sleep because the rapidly melting ice must be constantly replaced. Second, and, more importantly, it fails to constantly and uniformly cool all of the oral tissues that are prone to form inflammation. The known method does not maintain the oral tissues at a constant desired temperature for the duration of extended treatments, and mucositis and oral sores inevitably form and become a limiting problem that forces the chemotherapy dose to be reduced or the treatment discontinued. Although the patient may be able to withstand the lessened chemotherapy treatment, its effectiveness is limited and the cancer may grow at an uncontrollable rate despite the treatment.

Thus, in view of the inadequacies of the known method, there has been a need for an oral therapeutic apparatus, and a method of using the device, for effectively cooling selected oral tissues to reduce absorption of the chemotherapy agent and the subsequent formation of inflammation and oral sores, throughout extended periods of chemotherapy treatment. Such a device would reduce or eliminate the problem that have not been overcome by the known method and have reduced the effectiveness of previous chemotherapy treatments. Furthermore, there has been a need for an oral device that remains comfortable to the patient throughout the length of any treatment so that relaxation and even sleep can be obtained.

The present invention provides a solution to the above problems.

SUMMARY OF THE INVENTION

The invention is directed to a mouth piece for cooling of oral tissue of a patient during chemotherapy treatment. The mouth piece includes a malleable top element configured to rest adjacent at least major surfaces of the upper gums and teeth of a patient's mouth in a close-fitting relationship. The mouth piece further includes a malleable bottom element configured to rest adjacent to at least major surfaces of the lower gums and teeth of a patient's mouth in a close-fitting relationship. The top element is integral with or connected to the bottom element to permit emplacement in the mouth as a one-piece unit. The mouth piece further includes an aperture positioned in a frontal location that permits a patient to breathe through the mouth when the mouth piece is emplaced within the mouth in said operative close-fitting relationship. The mouth piece further includes a cooling medium contained within the top element and the bottom element and able to retain a cooling environment within the mouth sufficient to reduce capillary blood flow to the patient's mouth.

In another embodiment of the invention, the mouth piece includes an external chamber extending from the front of the mouth piece for storing a cooling medium comprised of a salt water solution. An aperture is positioned in a frontal location and extends through the external chamber that permits a patient to breathe through the mouth when the mouth piece is emplaced within the mouth in an operative close-fitting relationship. A series of bladders are positioned within the top element and the bottom element, wherein the bladders are connected to the external chamber for receiving the cooling medium which flows throughout the top element and the bottom element and for retaining a cooling environment within the mouth sufficient to reduce capillary blood flow to the patient's mouth.

In another embodiment, the external chamber and the elements that fit within the mouth are separable thus permitting coolants to be cooled as further described herein and introduced into the elements within the mouth, thus permitting the elements within the mouth to be sized best suited to the patient.

For example, the mouth piece can include mating elements which are dimensioned and configured to permit a proximal end of the first external chamber to be removably attached to the front of the mouth piece. The mating elements can include tongue and groove mating surfaces to permit a removable snap fit attachment. Alternatively, the mating elements include threaded mating surfaces to permit a removable screw fit attachment.

In one embodiment, at least one valve is fixedly positioned between the bladders and the external chamber for controlling the flow of the cooling medium. The at least one valve can be a duck bill valve, including a flexible tunnel that is configured to open when pressure is applied by the flow of the cooling medium. Other types of valves can be utilized with the invention, including one-way type valves. In other embodiments, the valves can include handles that are adjustable by a user to open and close them. In other embodiments, the valves can include ball valves.

In one embodiment, the first external chamber is positioned between the mouth piece and the second chamber. In another embodiment, the first external chamber includes a cavity forming a distal opening that is configured and dimensioned to receive the second chamber in a nested arrangement. Each of the first external chamber and the second chamber can include tapered proximal end portions.

In another embodiment, a support device is utilized for supporting the mouth piece having an external chamber. The device includes a sling having a surface for receiving the external chamber. The device further includes at least two support legs extending from the sling, wherein the support legs are configured to rest on a rigid surface for supporting the external chamber during use. Preferably, the support legs are configured to telescope and adjust to accommodate various environments and provide sturdy support.

In another embodiment, the mouth piece includes a malleable top element configured to rest adjacent at least major surfaces of the upper gums and teeth of a patient's mouth in a close-fitting relationship. The mouth piece includes a malleable bottom element configured to rest adjacent at least major surfaces of the lower gums and teeth of a patient's mouth in a close-fitting relationship. The top element is integral with or connected to the bottom element to permit emplacement in the mouth as a one-piece unit. An external chamber extends from the front of the mouth piece for storing a cooling medium comprised of a first solution having a freezing temperature below 0 degrees C. A bladder is positioned inside the external chamber for storing a second solution having a freezing temperature above the freezing point temperature of the first solution to assist in cooling the first solution. The first solution flows throughout the top element and the bottom element for retaining a cooling environment within the mouth sufficient to reduce capillary blood flow to the patient's mouth.

BRIEF DESCRIPTION OF THE DRAWINGS

In the accompanying drawings:

FIGS. 2-5 illustrate a first embodiment of the invention, wherein:

FIG. 2 is a cross-sectional view of a mouth piece taken in the direction of line 2-2 of FIG. 1, in accordance with the first embodiment;

FIG. 3 is a front, top, and left perspective view of the mouth piece of FIG. 2, wherein the cooling medium bladders for the upper gums are shown;

FIG. 4 is a top view of the mouth piece of FIG. 2 illustrating a plurality of bladders housing the cooling medium;

FIG. 5 is a side elevation view of the inside surface of the right upper outer wall of the mouth piece of FIG. 2 illustrating two rows of bladders being separated by a row of air pockets;

FIGS. 6-10 illustrate a second embodiment of the invention, wherein:

FIG. 6 is a cross-sectional view of a mouth piece taken in the direction of line 2-2 of FIG. 1, in accordance with the second embodiment;

FIG. 7 is a front, top, and left perspective view of the mouth piece of FIG. 6, wherein a single U-shaped bladder for insulating the upper teeth is shown;

FIG. 8 is a top view of the mouth piece of FIG. 2 illustrating the biting surface of the U-shaped upper insulation bladder;

FIG. 9 is a front, top, and left perspective view of the mouth piece of FIG. 6, further comprising an expandable upper wall for contacting the roof of the mouth; and FIG. 10 is a front, top, and left perspective view of the mouth piece of FIG. 9, further comprising four flexible arms for contacting the corners of the mouth;

FIGS. 11-14 illustrate a third embodiment of the invention, wherein:

FIG. 11 is an illustrational view of a mouth piece located within the mouth of a patient undergoing chemotherapy treatment, wherein an external chamber extends from the front of the mouth piece;

FIG. 12 is a cross-sectional view of a mouth piece taken in the direction of line 12-12 of FIG. 11, in accordance with the third embodiment;

FIG. 13 is a front, top, and left perspective view of the mouth piece of FIG. 12, wherein the cooling medium bladders for the upper gums are shown and are connected to the external chamber;

FIG. 14 is a top view of the mouth piece of FIG. 12 illustrating a series of connected bladders for receiving the cooling medium which flows throughout the top element and the bottom element;

FIGS. 16-20 illustrate a fifth embodiment of the invention, wherein:

FIG. 16 is an illustrational view of a mouth piece located within the mouth of a patient undergoing chemotherapy treatment, wherein a removable external chamber extends from the front of the mouth piece;

FIG. 17 is a cross-sectional view of a mouth piece taken in the direction of line 17-17 of FIG. 16, in accordance with the fifth embodiment;

FIG. 18 is a front, top, and left side perspective view of the mouth piece of FIG. 16, wherein the cooling medium bladders for the upper gums are shown and are connected to the external removable chamber;

FIG. 19 is a top view of the mouth piece of FIG. 16 illustrating a series of connected bladders for receiving the cooling medium which flows throughout the top element and the bottom element;

FIG. 20A is a front, top, and left side perspective exploded view of the mouth piece of FIG. 16, wherein the external chamber is removed from the mouth piece;

FIG. 20B is a front and left side perspective exploded view of the proximal end of the external chamber showing a cylindrical member and valves for controlling the flow of the cooling medium;

FIGS. 21-22 illustrate a sixth embodiment of the invention, wherein:

FIG. 21 illustrates a front, top, and left perspective view of the mouth piece of FIG. 12, wherein the cooling medium bladders for the upper gums are shown and are connected to the external chamber, wherein the external chamber includes a salt water chamber and a plurality of pure water capsules that move freely inside the salt water chamber and flow freely through the cooling medium bladders;

FIG. 22 is a top view of the mouth piece of FIG. 21 illustrating a series of connected bladders for receiving both the salt water cooling medium and the pure water capsules which flow freely throughout the top element and the bottom element;

FIGS. 24-34 illustrate an eighth embodiment of the invention, wherein:

FIG. 24 is an illustrational view of a mouth piece located within the mouth of a patient undergoing chemotherapy treatment, wherein an external chamber extends from the front of the mouth piece;

FIG. 25 is a cross-sectional view of a mouth piece taken in the direction of line 25-25 of FIG. 24, in accordance with the eighth embodiment;

FIG. 26 is a right side perspective exploded view of the mouth piece of FIG. 24, wherein the bladder is shown positioned for insertion between the mouth piece and the external chamber;

FIG. 27 is a right side perspective exploded view of the mouth piece of FIG. 24, wherein the bladder is shown positioned for insertion between the external chamber and a cap;

FIG. 28 is a right side perspective exploded view of the mouth piece of FIG. 24, showing the proximal wall of the mouthpiece that connects the top element and the bottom element;

FIG. 29 is a right side perspective exploded view of the mouth piece of FIG. 24, showing the bladder inserted inside the external chamber;

FIG. 30 is a top view of the mouth piece of FIG. 24 illustrating the bladder for receiving the cooling medium which flows throughout the top element and the bottom element;

FIGS. 31-32 are intra oral infrared temperature images showing the cooling effects of the mouth piece on a first test subject;

FIGS. 33-34 are intra oral infrared temperature images showing the cooling effects of the mouth piece on a second test subject.

DETAILED DESCRIPTION OF THE PREFERRED EMBODIMENTS

The present invention will now be described in detail with reference to the drawings.

Figure 1:
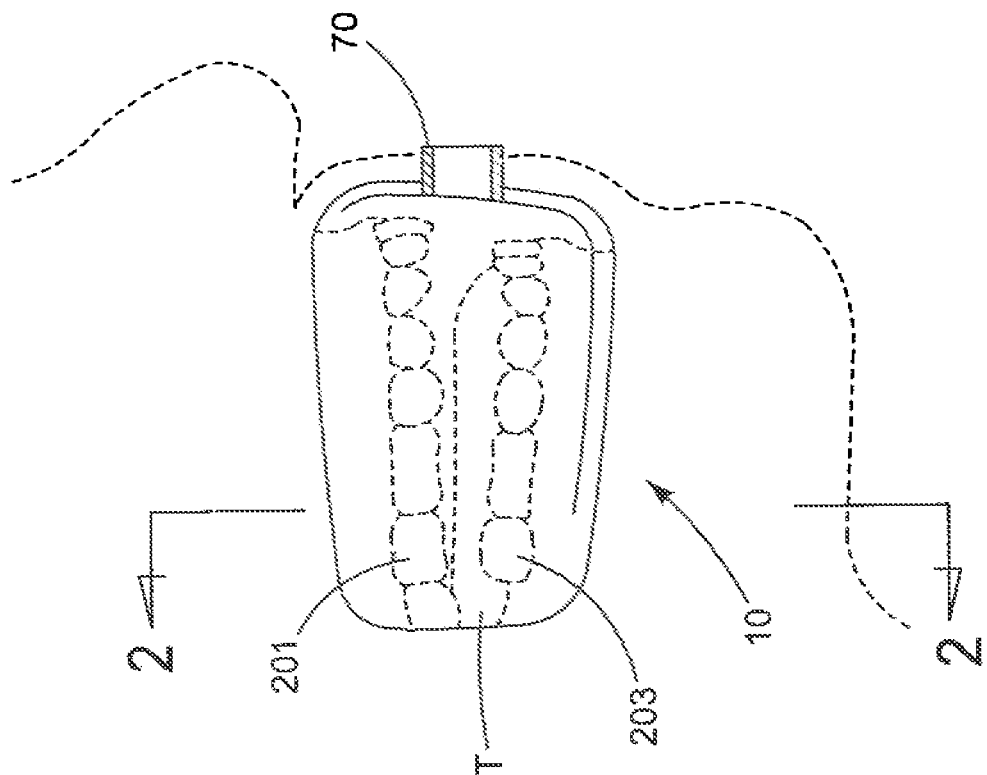
FIG. 1 is an illustrational view of a mouth piece in accordance with the invention located within the mouth of a patient undergoing chemotherapy treatment.
Figure 2:
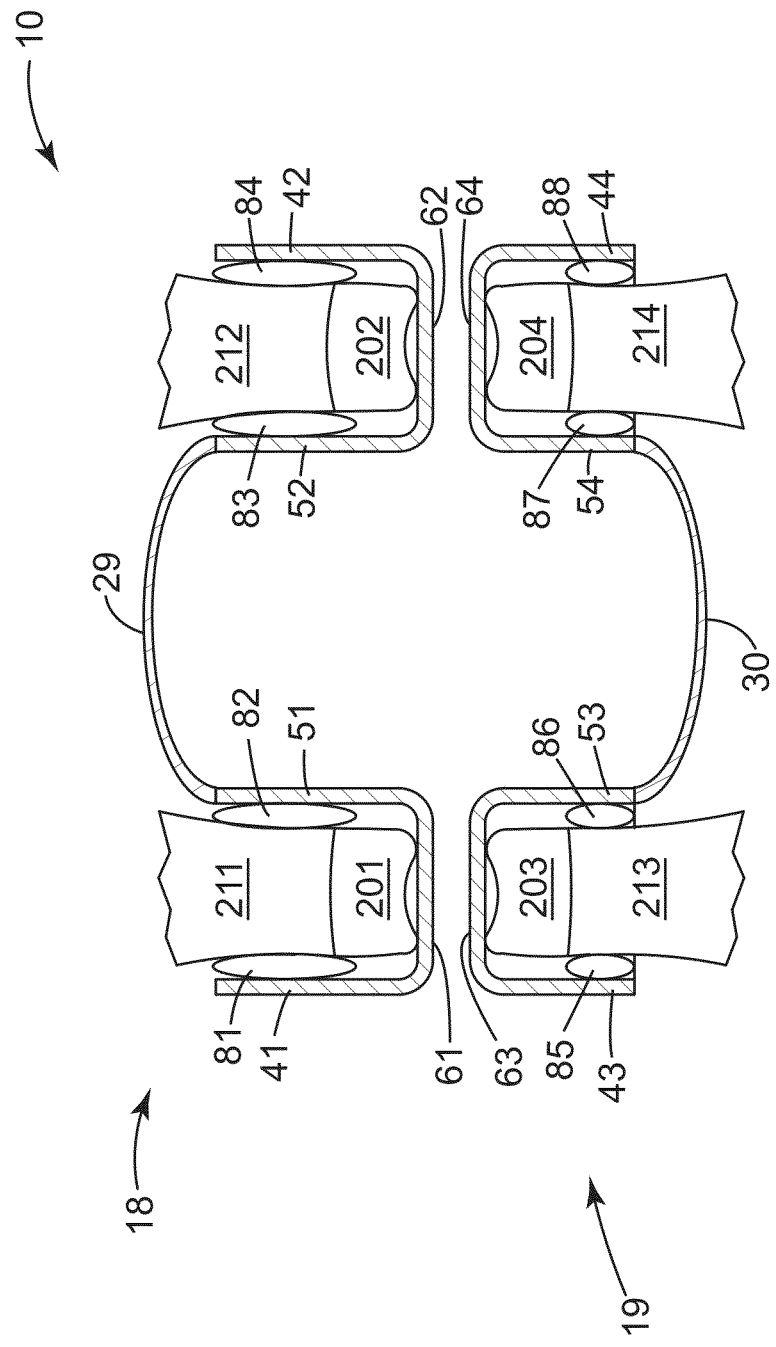
Figure 6:
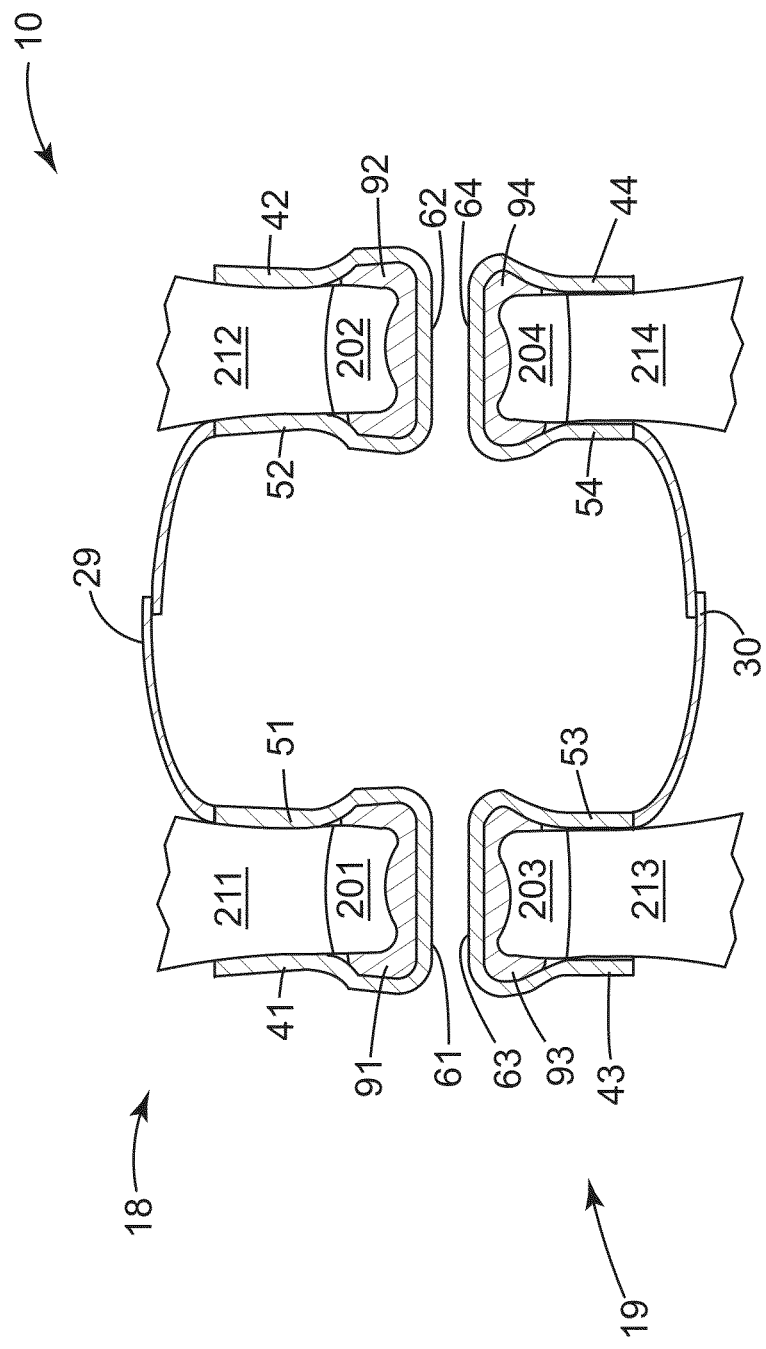

FIG. 1 illustrates a mouth piece 10 in accordance with the present invention which is located within the mouth of a patient undergoing chemotherapy treatment. As depicted in FIGS. 2 and 6, the therapeutic device is engaged simultaneously by the upper teeth 201 and 202 and lower teeth 203 and 204 of the patient, and includes an aperture 70 in a frontal location that permits the patient to breathe through the mouth when the mouth piece is emplaced with the mouth in an operative close-fitting relationship. In one embodiment, a flexible tube (not shown) can be inserted through or otherwise connected with the aperture 70 and positioned inside the patient's mouth to assist the patient with inhaling air from outside the mouth while breathing comfortably. In another embodiment, this flexible tube can be used to supply oxygen to the patient if medically warranted.

FIGS. 2-5 illustrate a first embodiment of the invention, wherein the mouth piece 10 is composed of a material that is malleable and biocompatible with the patient's oral tissues and can be used to form the device according to the size and shape of the patient's mouth as will be described in greater detail below. Suitable materials include, for example, acrylic, plastic, silicon and rubber. Unlike the second embodiment of the invention described below, the material of the mouth piece itself is not intended to be a cooling medium, but rather forms a framework with which to house bladders or other elements that are configured to act as the cooling medium as will be discussed below.

The mouth piece includes a top element 18 and a bottom element 19, which collectively provide total mouth coverage during chemotherapy treatment. The top element 18 is integral with or connected to the bottom element 19 to permit emplacement in the mouth as a one-piece unit. The top element 18 consists of a malleable material and is configured to rest adjacent at least major surfaces of the upper gums 211 and 212 and upper teeth 201 and 202 of a patient's mouth in a close-fitting relationship. The bottom element 19 consists of a malleable material and is configured to rest adjacent at least major surfaces of the lower gums 213 and 214 and lower teeth 203 and 204 of a patient's mouth in a close-fitting relationship.

In one embodiment, the therapeutic device is formed by first making stone casts of the patient's teeth along with a bite registration. The casts are mounted on an articulator to simulate the patient's occlusal, and the articulator is adjusted to form a 4-6 mm vertical occlusal space.

Next, a buildup is initiated with the preferred therapeutic device. A wax pattern is fabricated and added to the buildup, which pattern defines the inner and outer walls of the mouth piece. The preferred material is added to enclose the wax pattern as well as the position of the aperture 70. The preferred material is allowed to harden or cure either at room temperature, or at an elevated temperature within a heating source such as a pressure pot.

The hardened device is then placed in boiling water or within a hot atmosphere such as in an oven to melt the wax pattern, and the wax is poured out to produce a hollow device. The device is then finished, shaped and contoured. Finally, to assure that the outer surface of the finished device properly conforms to the contour of the patient's mouth, it is placed therein to verify an accurate fit. The device must fit comfortably and not extend so far into the patient's mouth that it causes the patient to gag.

In another embodiment, the mouth piece material has sufficient malleability and is manufactured in a variety of sizes in order to fit the patient's mouth according to his or her size without the need for making a custom device each time from a stone cast as was described above. For example, the mouth piece can be offered in sizes small, medium, large, and extra-large. The mouth piece can include flexible inner and outer walls to self-adjust its configuration to the size and shape of a patient's mouth.

Referring to FIG. 2, a separate cooling medium is contained within the top element 18 and the bottom element 19 and is able to retain a cooling environment within the mouth sufficient to reduce capillary blood flow to the patient's mouth to prevent mouth sores and oral discomfort following chemotherapy treatment. The cooling medium can be housed in a plurality of bladders 81-88 located at predetermined locations along the inner cavities of the mouth piece. Prior to use, the mouth piece is stored in a freezer or other temperature controlled environment in order to cool the cooling medium to a desired temperature. Preferably, the cooling medium of the mouth piece is able to maintain the necessary temperature while the mouth piece is in the patient's mouth to cool the oral tissues throughout a portion of time of chemotherapy treatment, depending on the types of drugs being administered and their known effects on the gums and mouth of the patient. For example, during a two hour chemotherapy treatment session, only a fifteen minute portion of the treatment may cause adverse effects on the gums and mouth. Therefore, the mouth piece of the present invention can be inserted into the mouth of the patient during the time of the chemotherapy treatment when it is most needed, such that the cooling effect of the mouth piece can be maximized at the most effective time.

The cooling medium is positioned within the mouth piece in order to contact and cool selected oral tissues within the patient's mouth. The cooling medium also partially cools the mouth piece which functions as a heat sink for heat generated in the oral tissues. The cooling medium functions such that heat is continuously transferred away from the oral tissues and the device, to keep the oral tissues cold and prevent the device from significantly warming during the chemotherapy treatment. Significant warming of the therapeutic device would allow inflammation and oral sores to form and consequently force the treatment to be reduced or discontinued.

Preferably, the cooling medium is maintained at a temperature of approximately 0 degrees C. to approximately 5 degrees C. The cooling medium can be carried by the device in sealed chambers, and the device is cooled in a freezer or other cooling device to the proper temperature prior to use. The cooling medium may be a non-toxic gel or a like substance made by adding hydroxyethyl cellulose (CELLU-SIZE™), sodium polyacrylate, or vinyl-coated silica gel that can maintain its initial temperature.

FIG. 2 is a cross-sectional view taken in the direction of line 2-2 of FIG. 1. The patient's right upper teeth 201 and right upper gums 211 engage the top right walls 41, 51 and 61, which collectively form a U-shaped cavity. Bladders 81 and 82 are attached to the vertical walls 41 and 51, respectively, and house the cooling medium as described above. The bladders are dimensioned to rest adjacent at least major surfaces of the right upper gums 211, as shown in FIG. 2. Similarly, the other remaining quadrants of the patient's mouth are treated in the same manner as described above and therefore do not require further discussion.

Figure 3:
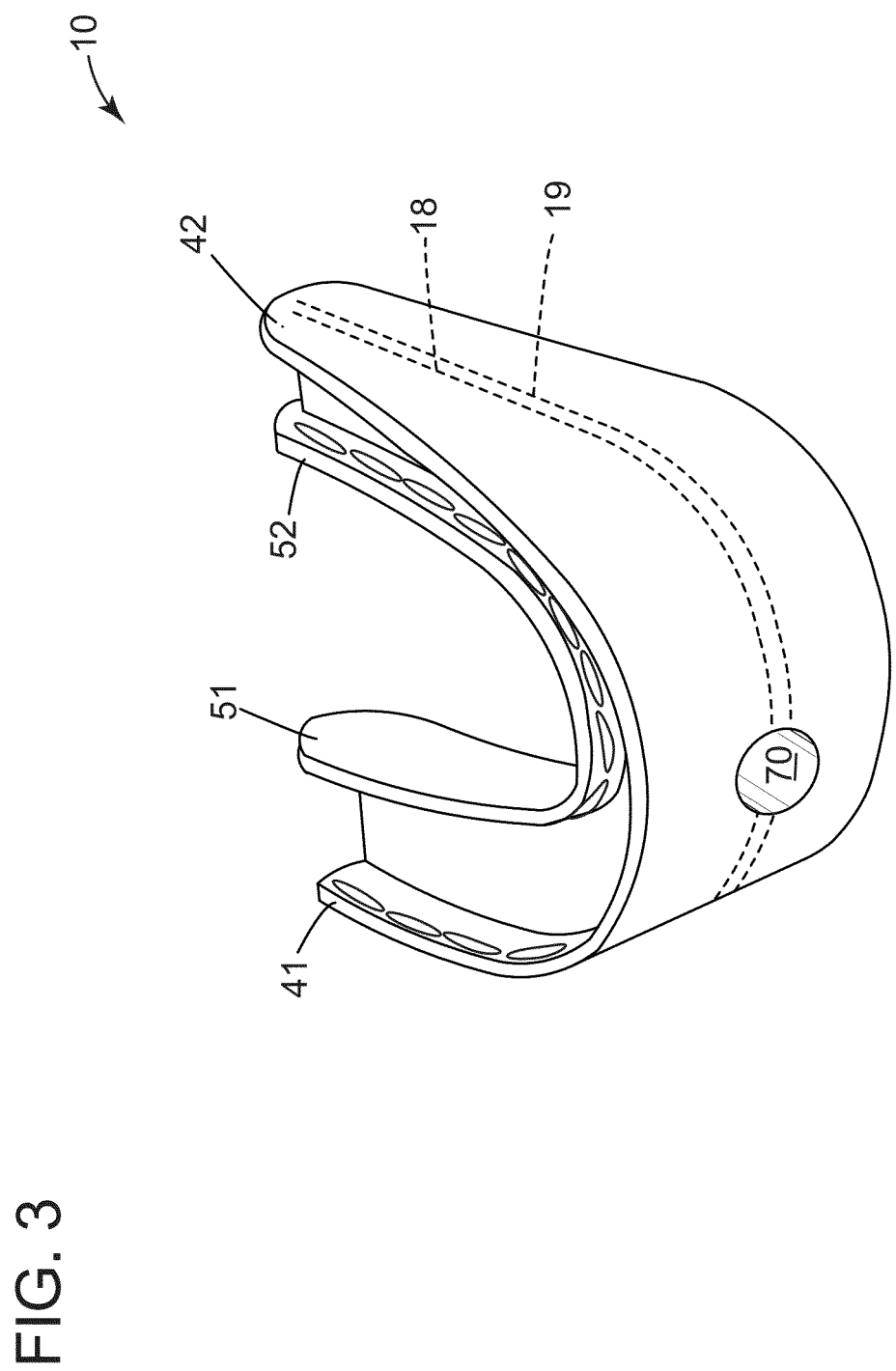

FIG. 3 illustrates a front, top, and left perspective view of the mouth piece, wherein the cooling medium bladders for the upper gums are shown. An aperture 70 is positioned in a frontal location that permits a patient to breathe through the mouth when the mouth piece 10 is emplaced within the mouth in the operative close-fitting relationship. Although the aperture 70 is illustrated as a single aperture, in other embodiments of the invention more than one aperture can be included. As illustrated, the top element 18 is integral with the bottom element 19 along their adjacent surfaces, collectively forming a single continuous side wall there between and permitting emplacement in the mouth as a one-piece unit. In other embodiments, the top element 18 can be hingedly connected to the bottom element 19 at the distal ends adjacent the joint of the jaw bones. In this embodiment, the patient can open and close his mouth while maintaining the cooling medium in contact with the top and bottom gums and teeth.

Figure 4:
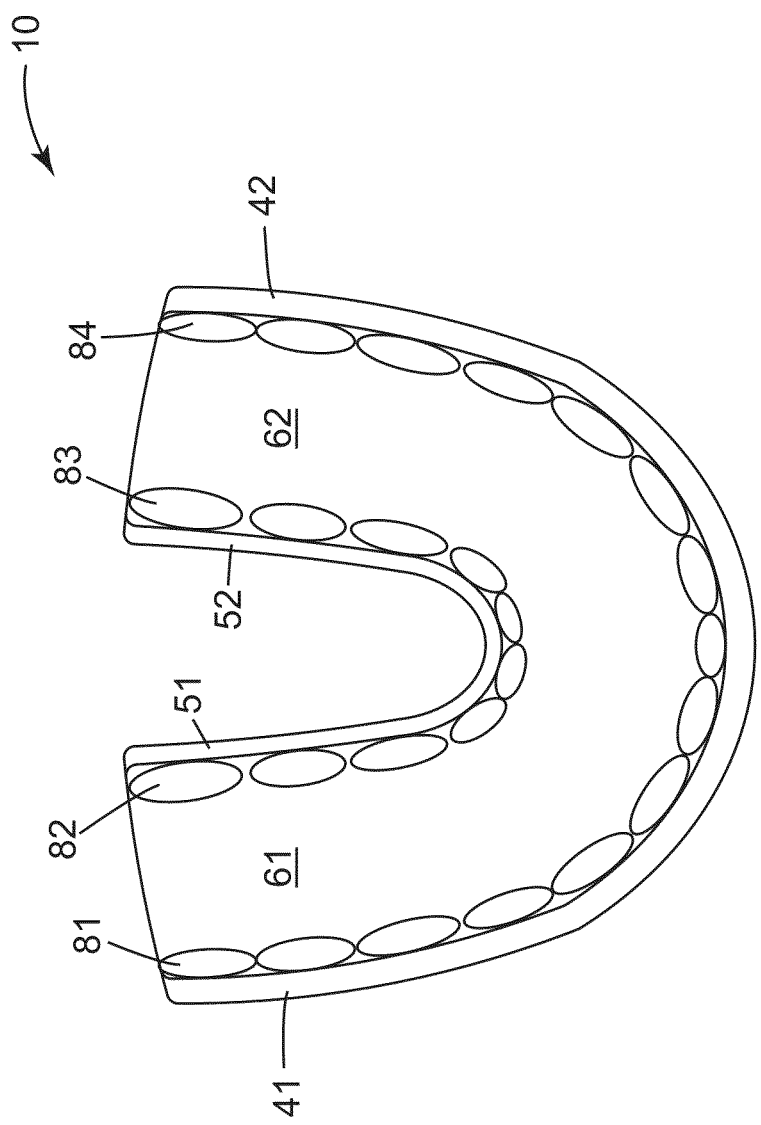

FIG. 4 is a top view of the mouth piece illustrating the plurality of bladders housing the cooling medium. In the illustrated embodiment, several discreet cooling chambers (bladders) 81-84 are provided along the interior walls of the mouth piece 10. The distribution of the cooling medium between several discreet chambers provides a malleable surface for contacting the gums of the patient without interfering with the breathing hole 70. The number and sizes of the discreet chambers can vary depending on the overall size of the mouth piece and the particular patient being treated. Preferably, each chamber is fixedly attached to the mouth piece with an appropriate adhesive or other means to prevent its dislodgement during use. In another embodiment, the chambers are removably attached and can be interchanged with various size bladders to control the amount and timing of cooling; or to adjust the fit of the mouth piece for the user's unique dental anatomy. For example, patients may have one or more teeth that are recessed or crooked from the adjacent teeth and a smaller or larger bladder can be fitted in this location of the mouth piece to accommodate for this discrepancy and therefore create more of a custom fit.

Figure 5:
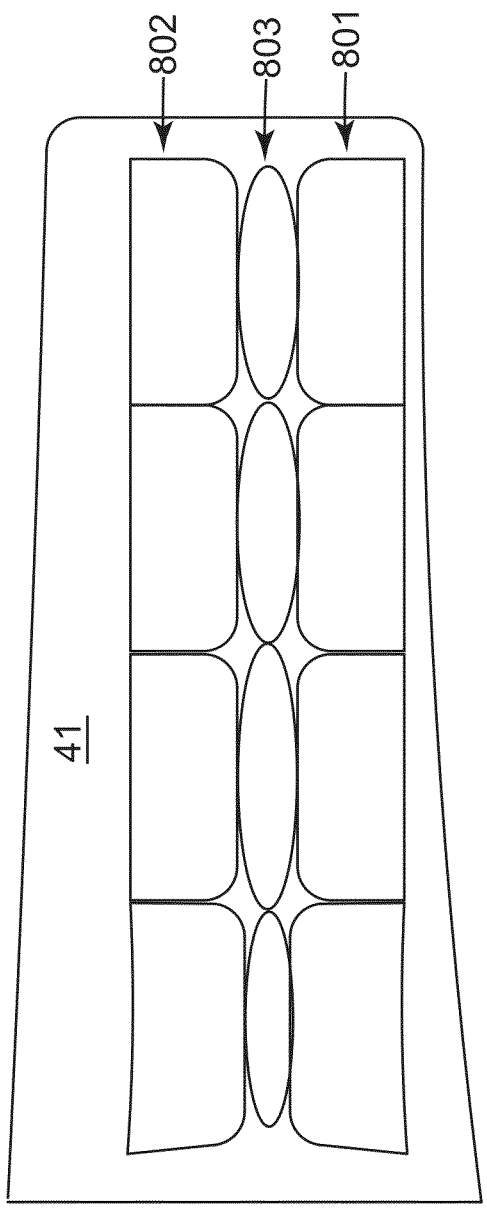

FIG. 5 is a side elevation view of the inside surface of the right upper outer wall 41 of the mouth piece illustrating two rows of bladders being separated by a row of air pockets. A first row of bladders 801 is positioned near the bottom and is intended to sit near the right upper teeth 201 (see FIG. 2) of the patient. A second row of bladders 802 is positioned near the top and is intended to sit near the right upper gums 211 (see FIG. 2) of the patient. Different volumes and/or types of cooling materials can be positioned in the first and second rows, respectively, to provide various cooling zones for gums vs. teeth. For example, the first row of bladders 801 can contain a cooling medium that warms up faster and removes less heat from the teeth (thus cooling the teeth less), as compared with the cooling medium that is contained within the second row of bladders 802. This can also be accomplished by utilizing a rubber or plastic material with a low specific heat. In general, it is preferred that the teeth are cooled less than the gums of the patient, especially if the patient has sensitive teeth for a variety of reasons.

In another embodiment, a row of air pockets 803 is positioned between the first and second rows of bladders. The air pockets act to thermally separate the first and second rows of bladders 801 and 802 and minimize thermal transfer between them. In other embodiments, the row of air pockets is not included with the device. Other thermal barriers can be utilized in place of the row of air pockets.

In another embodiment, the mouth piece includes a separate cooling medium (not shown) along the outer lateral surfaces of the sidewalls of the mouth piece to make contact with the patient's cheeks and cool the oral tissues thereof and also cool the gums along the upper and lower jaw.

In another embodiment, the mouth piece includes cooling medium (not shown) along an optional upper wall 29 (see FIG. 2) which contacts the roof of the mouth, and along an optional lower wall 30 (see FIG. 2) which contacts the base of the mouth, and a portion of the interior walls contacting the tongue. These wall portions can be utilized to cool the surrounding roof and base of the mouth, and the tongue as well as the adjacent gums.

FIGS. 6-10 illustrate a second embodiment of the invention, wherein the mouth piece 10 itself is composed of a material that is not only malleable and biocompatible with the patient's oral tissues and can be used to form the device according to the size and shape of the patient's mouth, but wherein the material forming the mouth piece itself is intended to act as the cooling medium as will be described in greater detail below. The material forming the mouth piece may include a non-toxic gel or a like substance made by adding hydroxyethyl cellulose (CELLUSIZE™), sodium polyacrylate, or vinyl-coated silica gel that can maintain its initial temperature.

The mouth piece includes a top element 18 and a bottom element 19, which collectively provide total mouth coverage and cooling during chemotherapy treatment. The top element 18 is integral with or connected to the bottom element 19 to permit emplacement in the mouth as a one-piece unit. The top element 18 consists of a malleable material and is configured to rest adjacent at least major surfaces of the upper gums 211 and 212 and upper teeth 201 and 202 of a patient's mouth in a close-fitting relationship. The bottom element 19 consists of a malleable material and is configured to rest adjacent at least major surfaces of the lower gums 213 and 214 and lower teeth 203 and 204 of a patient's mouth in a close-fitting relationship.

FIG. 6 is a cross-sectional view taken in the direction of line 2-2 of FIG. 1. The patient's right upper teeth 201 and right upper gums 211 engage the top right walls 41, 51 and 61, which collectively form a U-shaped cavity. Because the mouth piece itself is the cooling medium, the additional bladders described with reference to FIGS. 2-5 above are not necessary and are not included. A U-shaped insulation bladder 91 is attached between the vertical walls 41 and 51, respectively, and is composed of a material that becomes warm very quickly after removing the mouth piece from its cooling storage device. The U-shaped insulation bladder 91 thereby substantially prevents the teeth from cooling during use of the mouth piece. The U-shaped bladder 91 is dimensioned to rest adjacent at least major surfaces of the right upper teeth 201, as shown in FIG. 6. Similarly, the other remaining quadrants of the patient's mouth are treated in the same manner as described above and therefore do not require further discussion.

Figure 7:
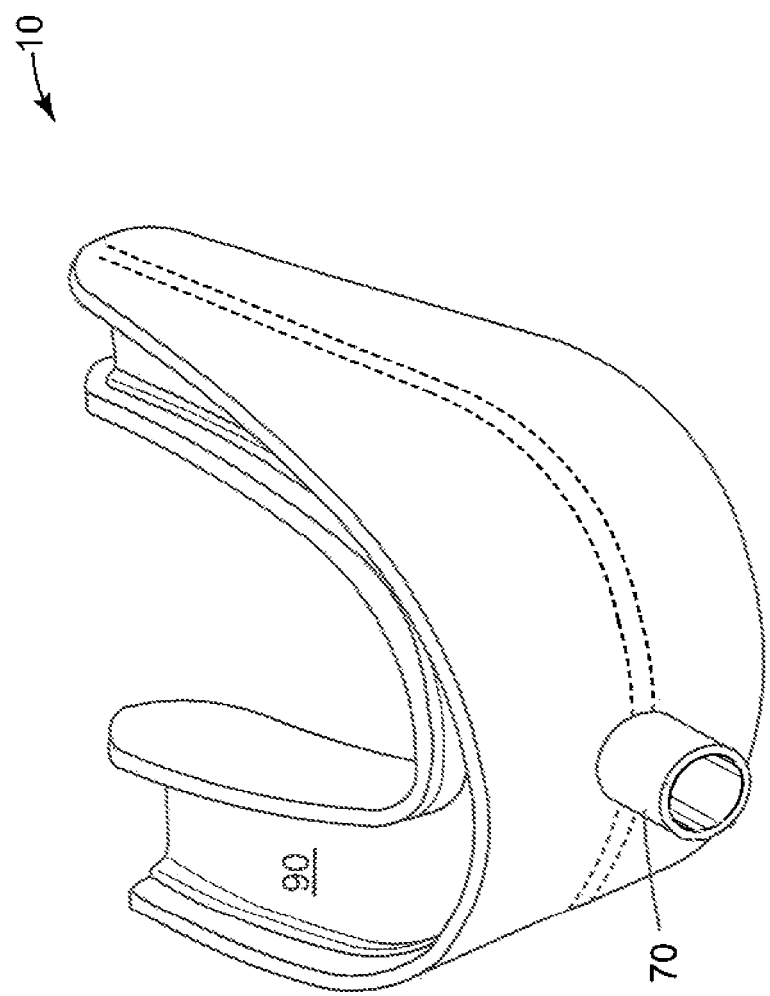

FIG. 7 illustrates a front, top, and left perspective view of the mouth piece, wherein a single U-shaped bladder 90 for insulating the upper teeth is shown as described above. In other embodiments, the U-shaped bladder can be comprised of multiple sections.

Figure 8:
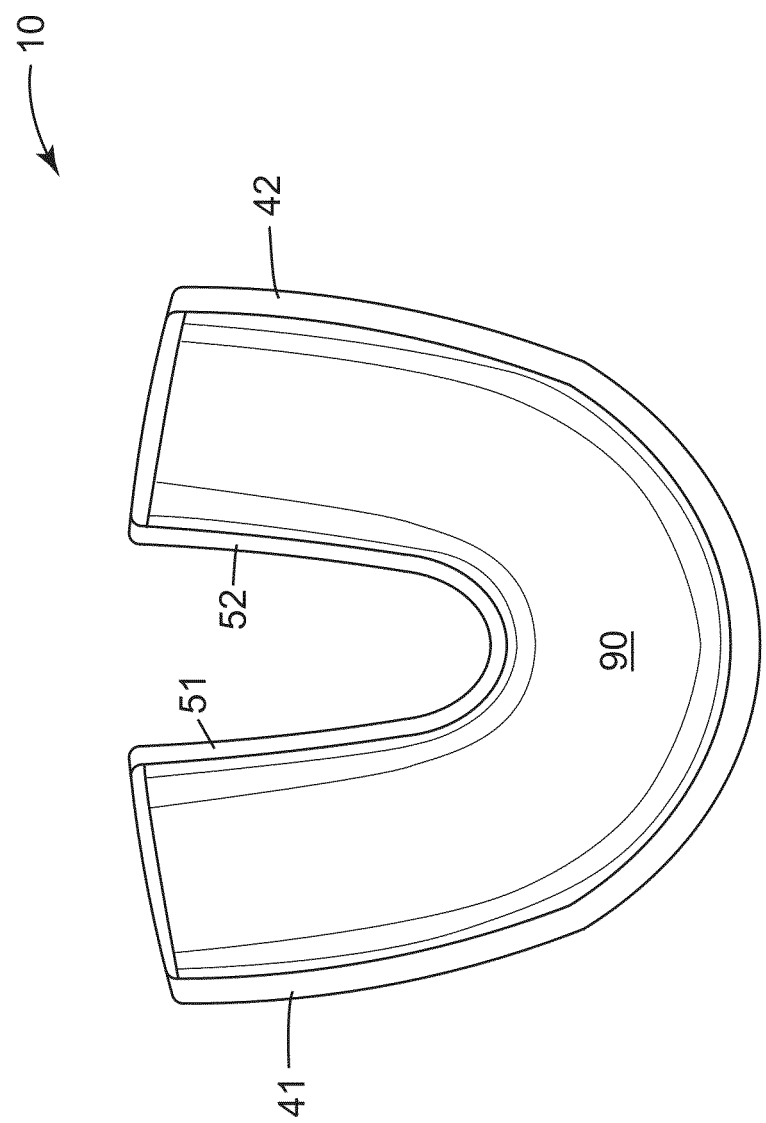

FIG. 8 is a top view of the mouth piece illustrating the biting surface of the U-shaped upper insulation bladder 90 as described above. The material forming the U-shaped insulation bladder can be malleable and provide a comfortable biting surface during insertion in the patient's mouth.

Figure 9:
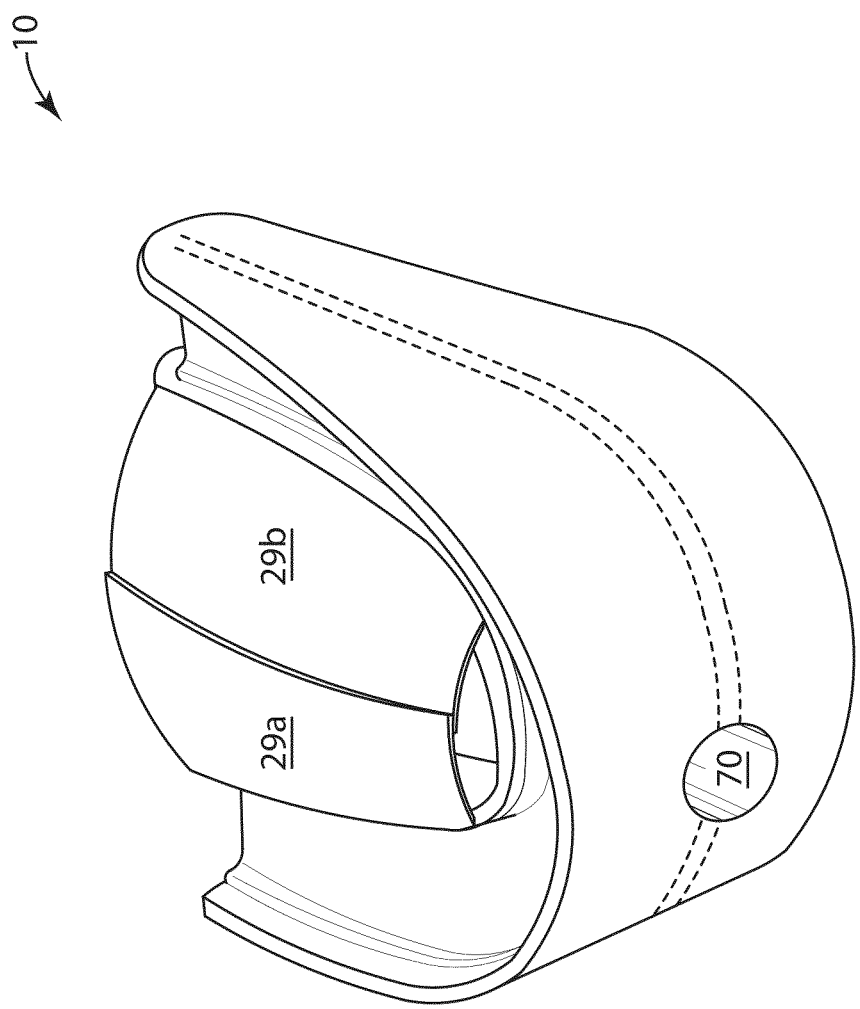

FIG. 9 is a front, top, and left perspective view of the mouth piece of FIG. 6, further comprising an expandable upper wall for contacting the roof of the mouth. In particular, the upper wall is formed by a first section 29a that extends vertically from the right upper inner wall 51 (see FIG. 6) and by a second section 29b that extends vertically from the left upper inner wall 52 (see FIG. 6) respectively of the mouth piece. The first section 29a slides over the second section 29b to form a generally continuous top surface for contacting the roof of the patient's mouth thereby also cooling this area during chemotherapy treatment. The first section 29a and second section 29b are composed of a similar cooling material as the rest of the mouth piece and can also include additional material and/or internal structural reinforcement to ensure that the top portion maintains suitable structural integrity and generally have an upward biasing force to maintain contact with the roof of the mouth. The top portion includes the ability to widen and narrow because of the overlapping arrangement of the first section 29a and second section 29b. Accordingly, the mouth piece can accommodate various size mouth widths while maintaining the ability to cool the roof of the patient's mouth.

Although not shown in perspective view, the bottom of the mouth piece includes a similar lower portion (see FIG. 6) configured to contact the bottom/floor of the patient's mouth, while not interfering with the frenulum of the tongue (also known as tongue web, lingual frenulum, or frenulum linguae) which is the small fold of mucous membrane extending from the floor of the mouth to the midline of the underside of the tongue.

Figure 10:
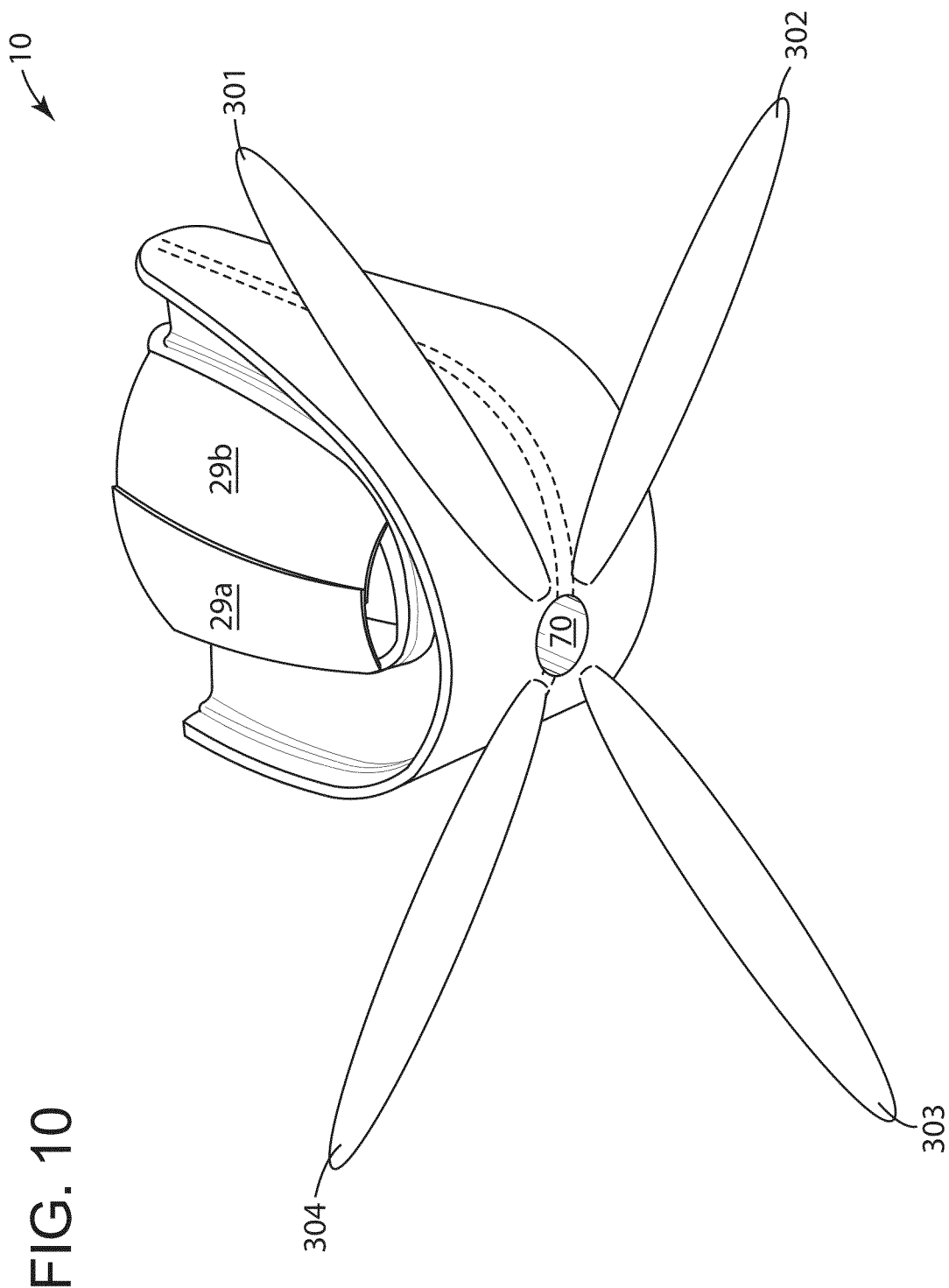

FIG. 10 is a front, top, and left perspective view of the mouth piece of FIG. 9, further comprising four flexible arms 301-304 configured to contact the corners of the mouth during use. Each flexible arm is attached at a proximal end near the aperture 70 positioned at the front of the mouth piece and extends out in a radial direction when the mouth piece is not positioned inside the patient's mouth. The flexible arms 301-304 are composed of a similar cooling material as the rest of the mouth piece and can also include additional material and/or internal structural reinforcement to ensure suitable structural integrity. For example, a resilient longitudinal core can be housed inside each flexible arm to provide the proper structural integrity and the proper flexibility. During use, the mouth piece 10 is inserted into the patient's mouth. Then each flexible arm is inserted and positioned into each corner of the patient's mouth. The flexible arms thereby provide additional cooling zones in the hard to reach areas located in the corners of the patient's mouth near the wisdom teeth. Accordingly, in this embodiment the mouth piece can accommodate various size mouths while maintaining the ability to cool the corners of the patient's mouth, including the gums and cheeks adjacent these areas of the mouth.

The therapeutic device in accordance with the present invention constantly and uniformly cools the patient's cheeks, gums, tongue, and roof and floor of the mouth. Because it closely conforms to the contour of the patient's mouth, it can be used for extensive treatments without causing discomfort. Furthermore, its uniform cooling action reduces or prevents the formation of inflammation and oral sores throughout extended chemotherapy treatments.

In another embodiment of the invention, a system for cooling of oral tissue of a patient during chemotherapy treatment is disclosed. The system includes a plurality of mouth pieces which are simultaneously cooled. During use, a first mouth piece is selected and inserted into the patient's mouth, while the remaining mouth pieces continue to be stored in a temperature controlled cooled environment. After a preselected time or after a preselected temperature of the mouth is reached, the first mouth piece is removed and replaced by a second mouth piece to regain the desired cooling effect that began to fade from the first mouth piece. In this way, a constant supply of cooled mouth pieces is available for the patient for use during chemotherapy treatment. For example, the plurality of mouth pieces can be stored in a refrigerator, freezer, cooling tub with ice, and the like and available to access within close proximity of the patient.

FIGS. 11-14 illustrate a third embodiment of the invention, wherein an external chamber 300 extends from the front of the mouth piece 10. An insulation wall 301 surrounds the external chamber 300 to help maintain a cold temperature of the liquid contents. The external chamber 300 preferably includes a salt water chamber 303 and a pure water chamber 304. A separation wall 302 provides a barrier between the salt water chamber 303 and the pure water chamber 304. In one embodiment, the salt water chamber 303 and the pure water chamber have surfaces that lie adjacent to each other, along the separation wall 302. The separation wall can be made of a flexible material, such as a thin rubber or plastic material. In another embodiment, the separation wall can be made of aluminum or other type of highly conductive material.

Although salt water and pure water are preferred because of their safety and ready availability, other materials which, like salt water, have a freezing point well below 0 degrees C. and pure water with a freezing point of 0 degrees C., other solutions in which the freezing point of one solution is close to 0 degrees C. and the other of which has a freezing point below 0 degrees C. can be substituted either for the salt water, pure water or both.

The mouth piece includes a top element 18 and a bottom element 19, which collectively provide total mouth coverage and cooling during chemotherapy treatment. The top element 18 is integral with or connected to the bottom element 19 to permit emplacement in the mouth as a one-piece unit. The top element 18 consists of a malleable material and is configured to rest adjacent at least major surfaces of the upper gums 211 and 212 and upper teeth 201 and 202 of a patient's mouth in a close-fitting relationship. The bottom element 19 consists of a malleable material and is configured to rest adjacent at least major surfaces of the lower gums 213 and 214 and lower teeth 203 and 204 of a patient's mouth in a close-fitting relationship.

Figure 11:
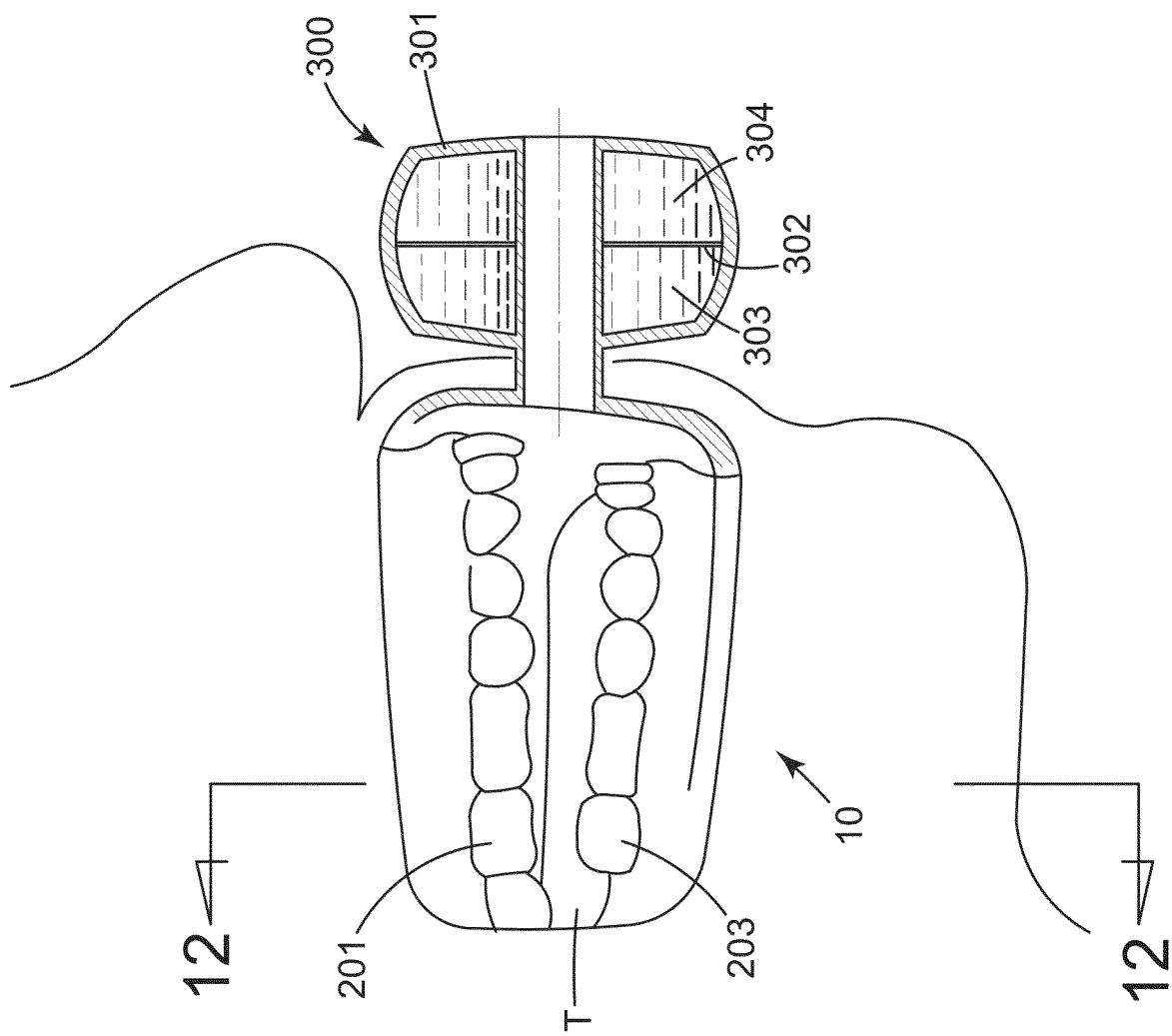
Figure 12:
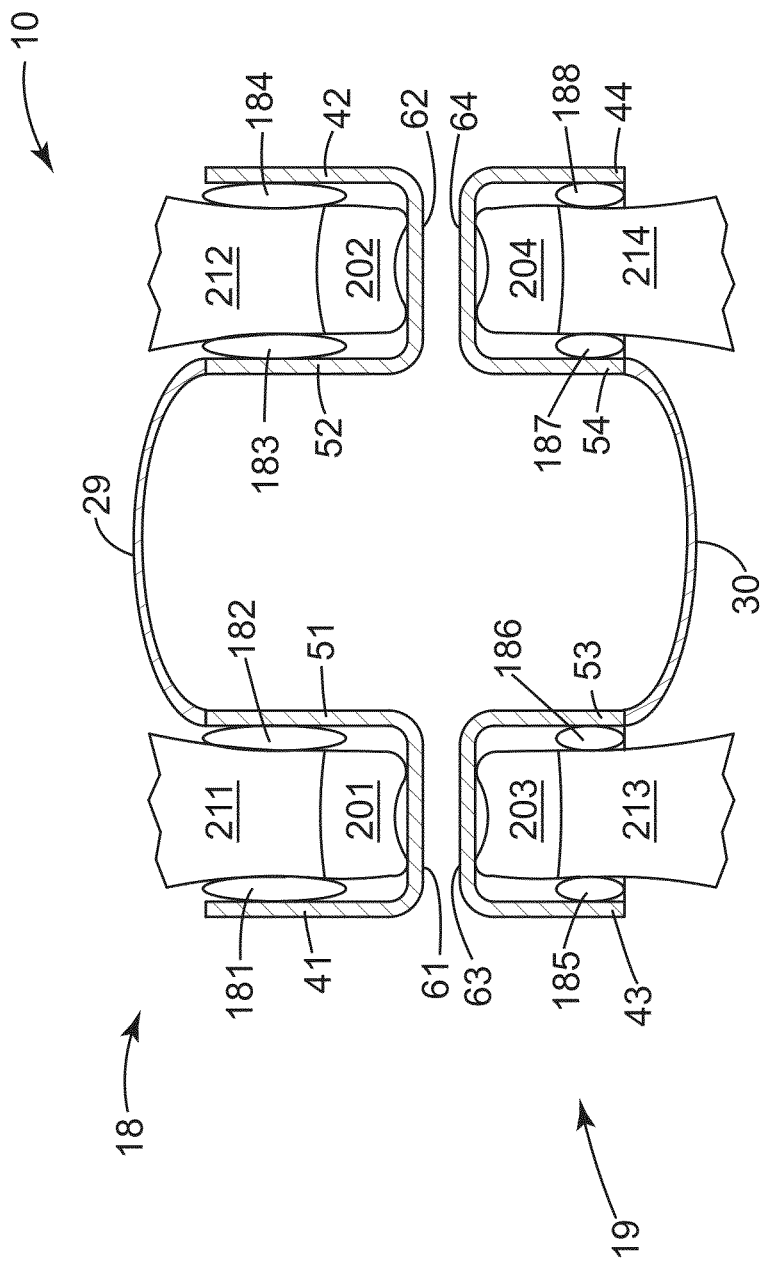

FIG. 12 is a cross-sectional view taken in the direction of line 12-12 of FIG. 11. The patient's right upper teeth 201 and right upper gums 211 engage the top right walls 41, 51 and 61, which collectively form a U-shaped cavity. Bladders 181 and 182 are attached to the vertical walls 41 and 51, respectively, and house the cooling medium as described above. The bladders are dimensioned to rest adjacent at least major surfaces of the right upper gums 211, as shown in FIG. 12. Similarly, the other remaining quadrants of the patient's mouth are treated in the same manner as described above and therefore do not require further discussion.

Figure 13:
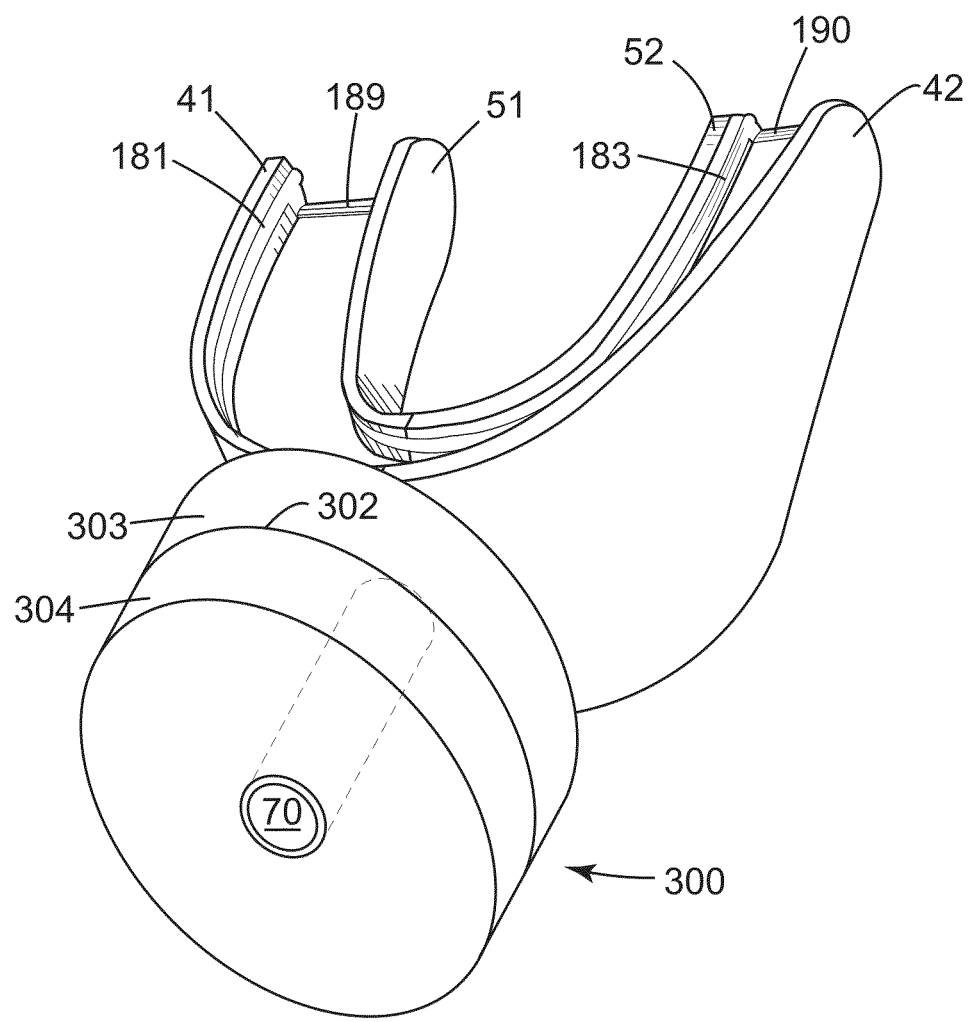

FIG. 13 illustrates a front, top, and left perspective view of the mouth piece, wherein the cooling medium bladders 181, 189, 183, and 190 for the upper gums are shown. An aperture 70 is positioned in a frontal location and extends through the external chamber 300 that permits a patient to breathe through the mouth when the mouth piece 10 is emplaced within the mouth in the operative close-fitting relationship. Although the aperture 70 is illustrated as a single aperture, in other embodiments of the invention more than one aperture can be included. The interior wall of the aperture 70 is made from a rigid or semi-rigid material, such as plastic, hard rubber, etc., in order to maintain its shape under the weight of the external chamber 300 without crimping. As illustrated, the top element 18 is integral with the bottom element 19 along their adjacent surfaces, collectively forming a single continuous side wall there between and permitting emplacement in the mouth as a one-piece unit. In other embodiments, the top element 18 can be hingedly connected to the bottom element 19 at the distal ends adjacent the joint of the jaw bones. In this embodiment, the patient can open and close his mouth while maintaining the cooling medium in contact with the top and bottom gums and teeth.

Figure 14:
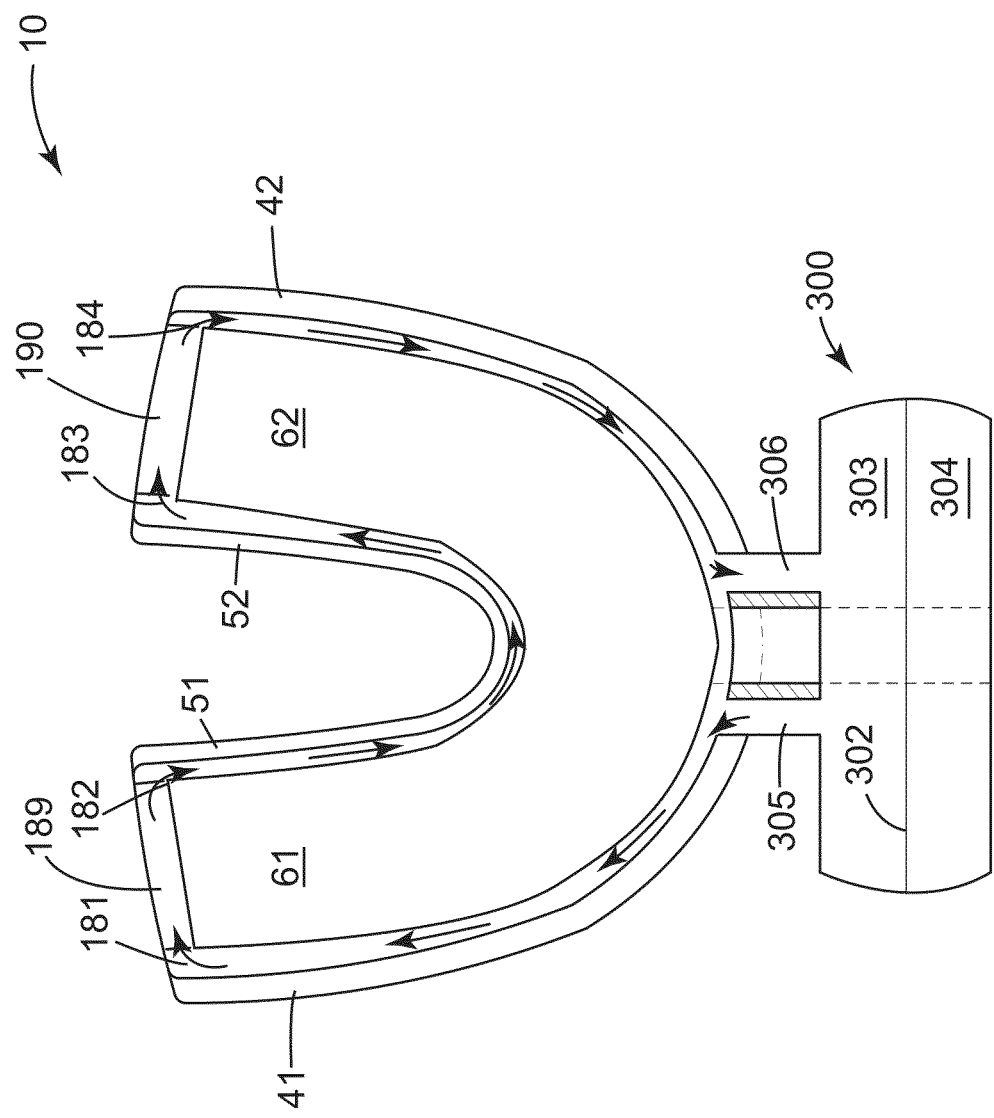

FIG. 14 is a top view of the mouth piece illustrating the plurality of bladders housing the salt water solution which flows from the salt water chamber 303 via one or more channels 305 and 306. The mouth piece and external chamber are kept in a freezer before use so that the water that is stored in the pure water chamber 304 is frozen. The pure water chamber 304 will provide a cooling effect for the salt water flowing through the bladders in the mouth piece as illustrated by the arrows in the drawing. In the illustrated embodiment, a series of cooling chambers (bladders) 181-184 are provided along the interior walls of the mouth piece 10. The distribution of the cooling medium between several connected chambers provides a malleable surface for contacting the gums of the patient without interfering with the breathing hole 70. The number and sizes of the discreet chambers can vary depending on the overall size of the mouth piece and the particular patient being treated. The series of bladders form a completely connected network. For example, bladder 189 is positioned at the rear surface of the mouth piece and connects bladder 181 to bladder 182. Similarly, bladder 190 is positioned at the rear surface of the mouth piece and connects bladder 183 to bladder 184. Preferably, each bladder is fixedly attached to the mouth piece with an appropriate adhesive or other means to prevent its dislodgement during use. In another embodiment, the chambers are removably attached and can be interchanged with various size bladders to control the amount and timing of cooling; or to adjust the fit of the mouth piece for the user's unique dental anatomy. For example, patients may have one or more teeth that are recessed or crooked from the adjacent teeth and a smaller or larger bladder can be fitted in this location of the mouth piece to accommodate for this discrepancy and therefore create more of a custom fit.

Figure 15:
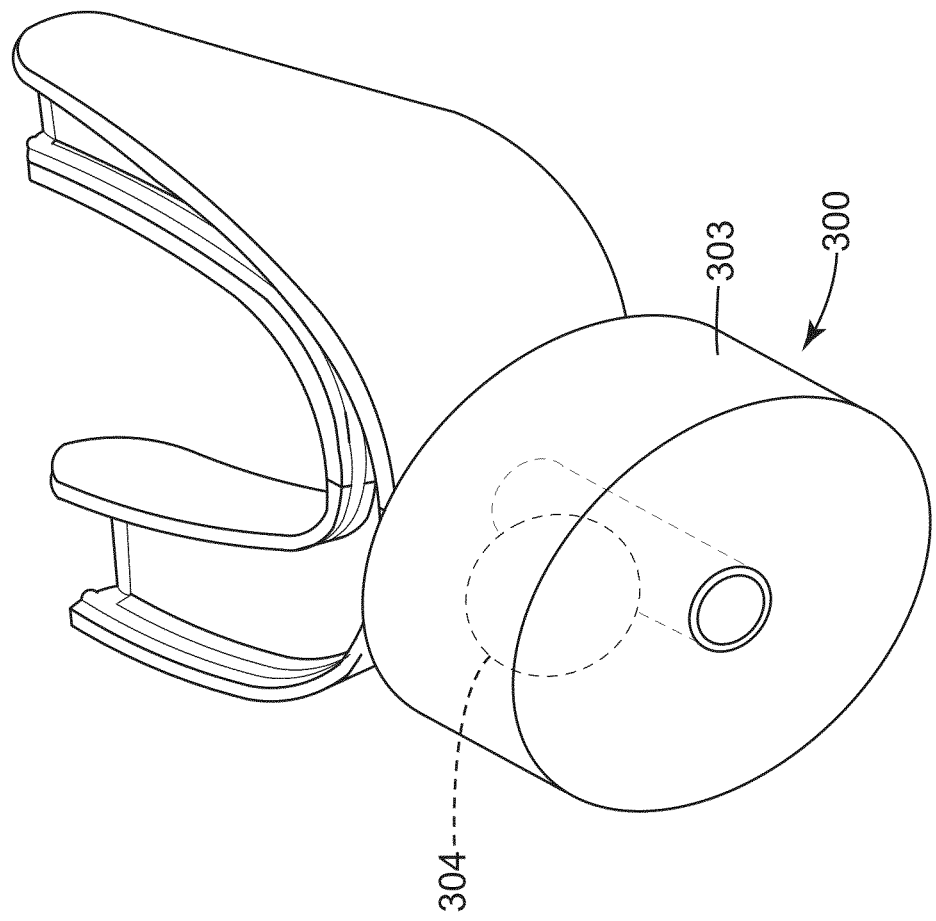
FIG. 15 illustrates a fourth embodiment of the invention, showing a front, top, and left perspective view of the mouth piece of FIG. 12, wherein the cooling medium bladders for the upper gums are shown and are connected to the external chamber, wherein the external chamber includes a salt water chamber and a pure water chamber that moves freely inside the salt water chamber.

FIG. 15 a fourth embodiment of the invention, showing a front, top, and left perspective view of the mouth piece of FIG. 12, wherein the cooling medium bladders for the upper gums are shown and are connected to the external chamber, wherein the external chamber includes a salt water chamber 303 and a pure water chamber 304 that moves freely inside the salt water chamber. In the example illustrated, the pure water chamber 304 is spherically-shaped, but other shapes can be employed. Furthermore, more than one water chamber 304 can be included with this embodiment of the invention.

The outer insulation wall of the external chamber 303 is selected to maintain its shape, yet also provides elasticity to allow a user to periodically squeeze the contents and assist the flow of the salt water solution through the series of bladders of the mouth piece.

In another embodiment (not shown), there is only a salt water chamber 303 and there is no pure water chamber 304. The size of the salt water chamber 303 can be adjusted depending on the amount and length of time that the cooling effect is required, without the need for a pure water (frozen) chamber.

In another embodiment (not shown), an adjustable support band is attached to the external chamber for wrapping around the users head to help support the weight of the external chamber. The support band can be secured via hook-and-loop fasteners, buckles, snaps, and the like.

Figure 16:
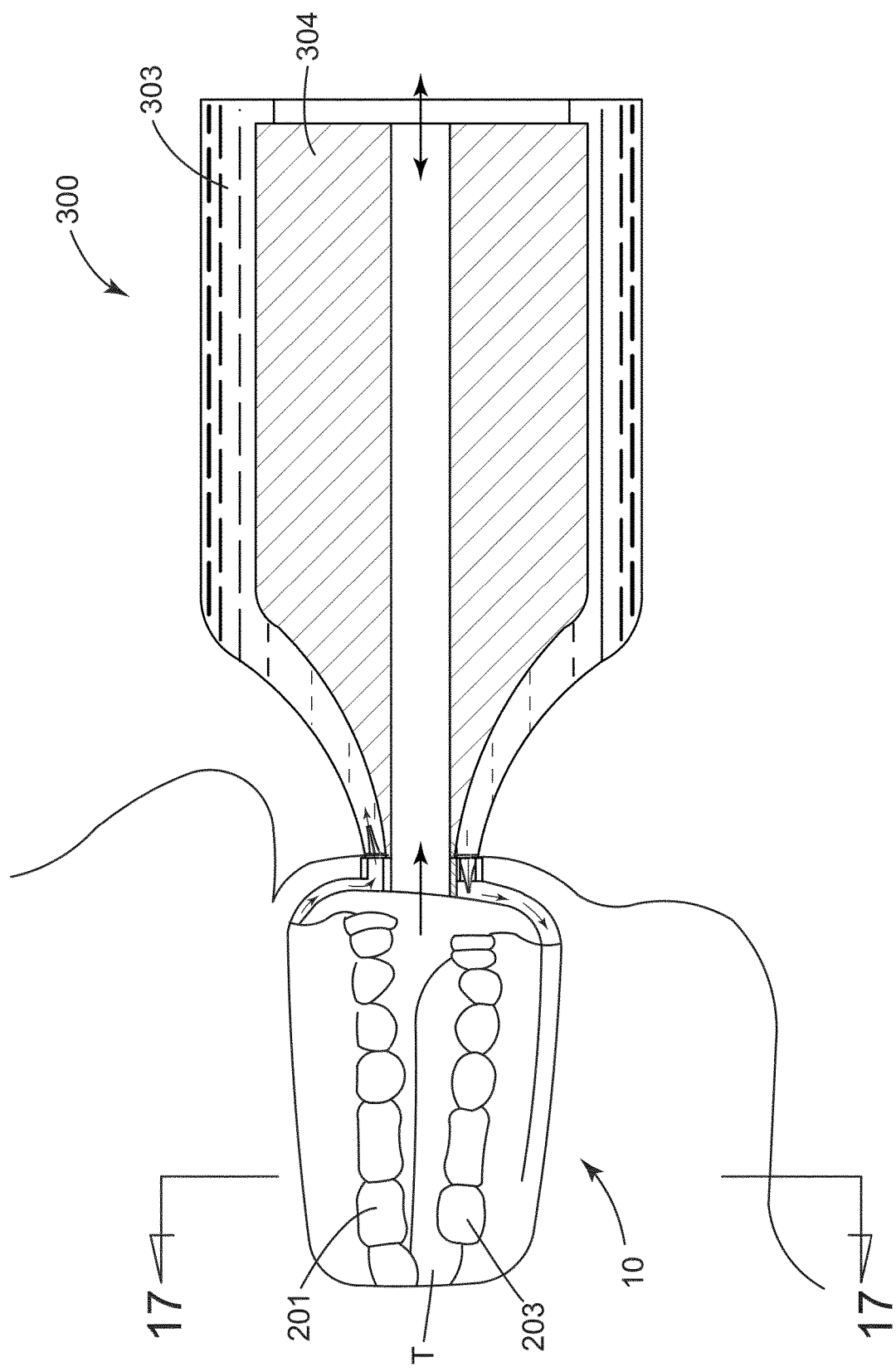

FIGS. 16-20 illustrate a fifth embodiment of the invention. FIG. 16 is an illustrational view of a mouth piece located within the mouth of a patient undergoing chemotherapy treatment, wherein a removable external chamber 300 extends from the front of the mouth piece.

The external chamber 300 preferably includes a salt water chamber 303 and a pure water chamber 304. An insulation layer (not shown) can be included to provide a barrier between the salt water chamber 303 and the pure water chamber 304.

Although salt water and pure water are preferred because of their safety and ready availability, other materials which, like salt water, have a freezing point well below 0 degrees C. and pure water with a freezing point of 0 degrees C., other solutions in which the freezing point of one solution is close to 0 degrees C. and the other of which has a freezing point below 0 degrees C. can be substituted either for the salt water, pure water or both.

The mouth piece includes a top element 18 and a bottom element 19, which collectively provide total mouth coverage and cooling during chemotherapy treatment. The top element 18 is integral with or connected to the bottom element 19 to permit emplacement in the mouth as a one-piece unit. The top element 18 consists of a malleable material and is configured to rest adjacent at least major surfaces of the upper gums 211 and 212 and upper teeth 201 and 202 of a patient's mouth in a close-fitting relationship. The bottom element 19 consists of a malleable material and is configured to rest adjacent at least major surfaces of the lower gums 213 and 214 and lower teeth 203 and 204 of a patient's mouth in a close-fitting relationship.

Figure 17:
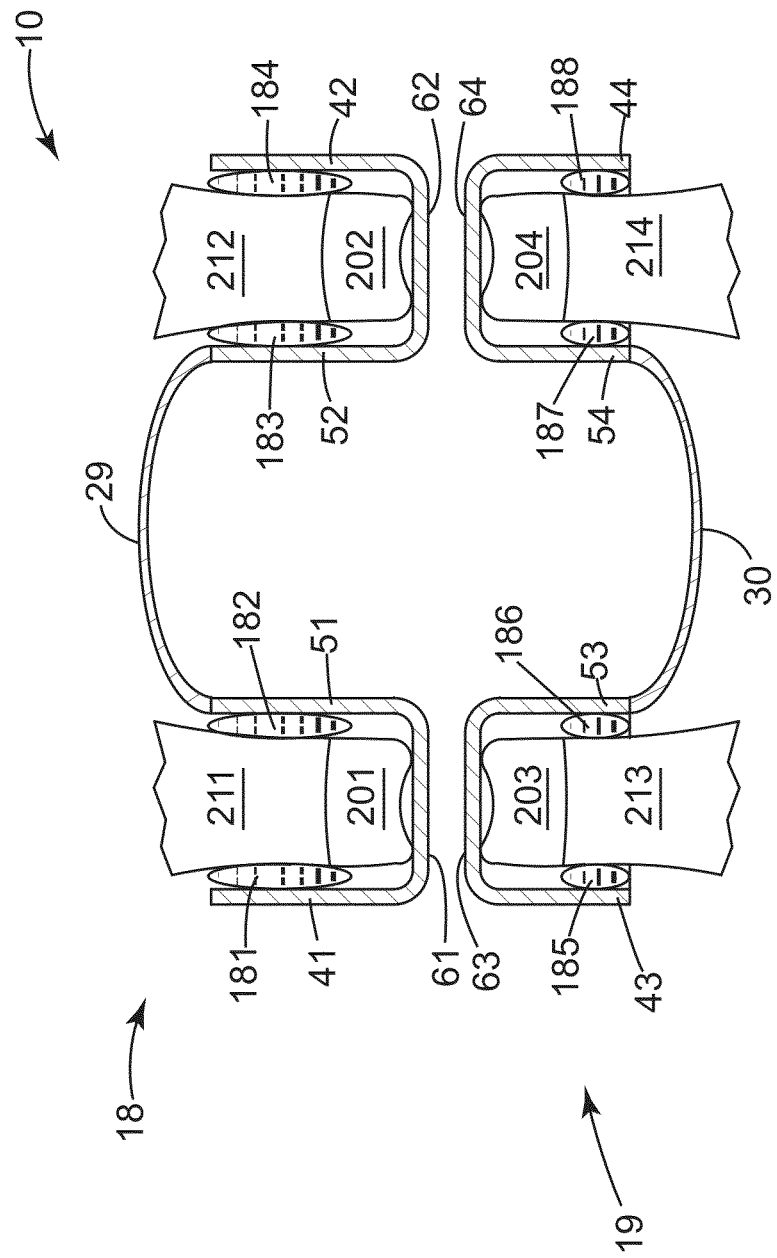

FIG. 17 is a cross-sectional view of a mouth piece taken in the direction of line 17-17 of FIG. 16, in accordance with the fifth embodiment. The patient's right upper teeth 201 and right upper gums 211 engage the top right walls 41, 51 and 61, which collectively form a U-shaped cavity. Bladders 181 and 182 are attached to the vertical walls 41 and 51, respectively, and house the cooling medium as described above. The bladders are dimensioned to rest adjacent at least major surfaces of the right upper gums 211, as shown in FIG. 17. Similarly, the other remaining quadrants of the patient's mouth are treated in the same manner as described above and therefore do not require further discussion.

Figure 18:
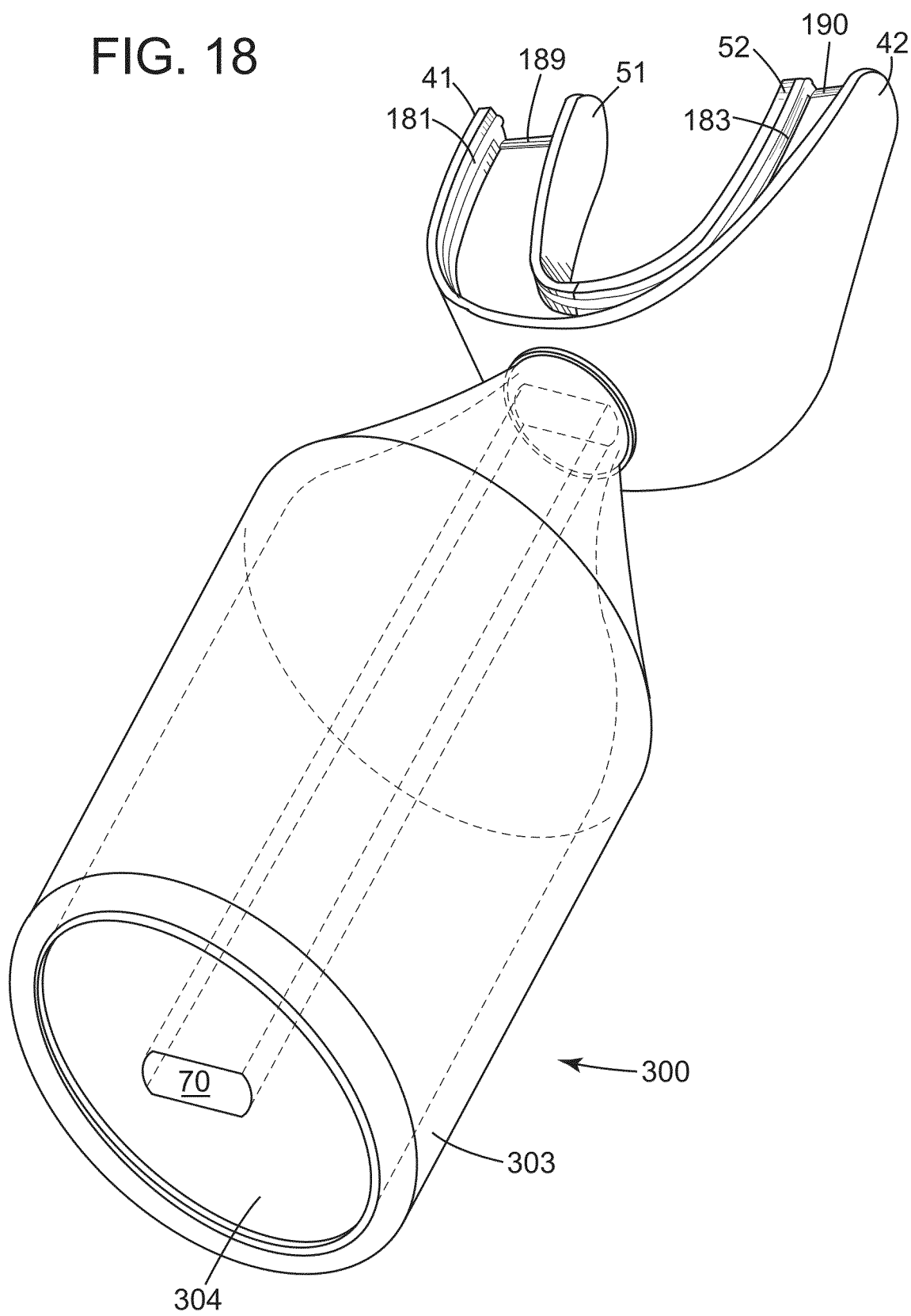

FIG. 18 is a front, top, and left side perspective view of the mouth piece of FIG. 16, wherein the cooling medium bladders 181, 189, 183, and 190 for the upper gums are shown and are connected to the external removable chamber. An aperture 70 is positioned in a frontal location and extends through the external chamber 300 that permits a patient to breathe through the mouth when the mouth piece 10 is emplaced within the mouth in the operative close-fitting relationship. Although the aperture 70 is illustrated as a single aperture, in other embodiments of the invention more than one aperture can be included. For all embodiments of the invention, the aperture 70 can be round, slotted, oval, rectangular, or any other shape. The interior wall of the aperture 70 can be made from a rigid or semi-rigid material, such as plastic, hard rubber, etc., in order to maintain its shape under the weight of the external chamber 300 without crimping. As illustrated, the top element 18 is integral with the bottom element 19 along their adjacent surfaces, collectively forming a single continuous side wall there between and permitting emplacement in the mouth as a one-piece unit. In other embodiments, the top element 18 can be hingedly connected to the bottom element 19 at the distal ends adjacent the joint of the jaw bones. In this embodiment, the patient can open and close his mouth while maintaining the cooling medium in contact with the top and bottom gums and teeth.

Figure 19:
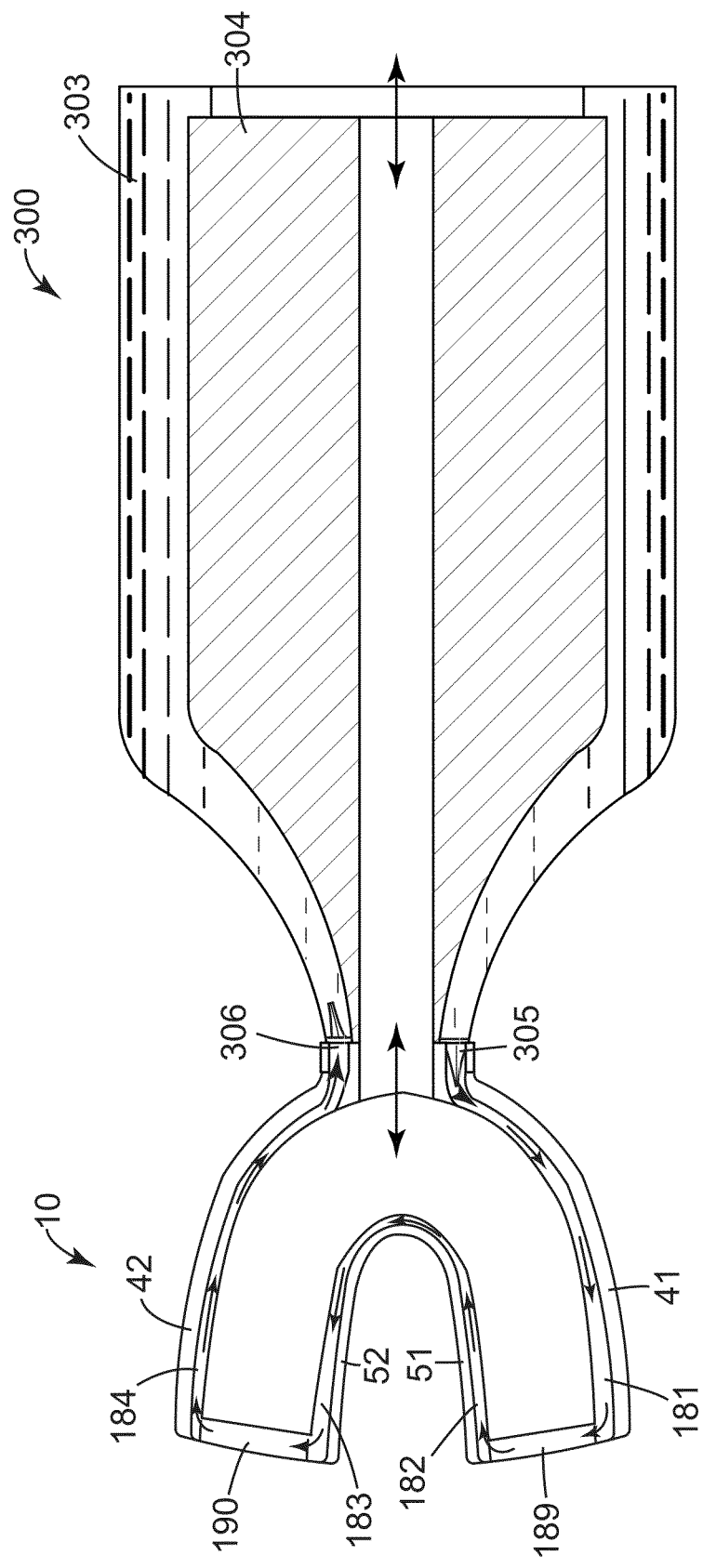
Figure 20:
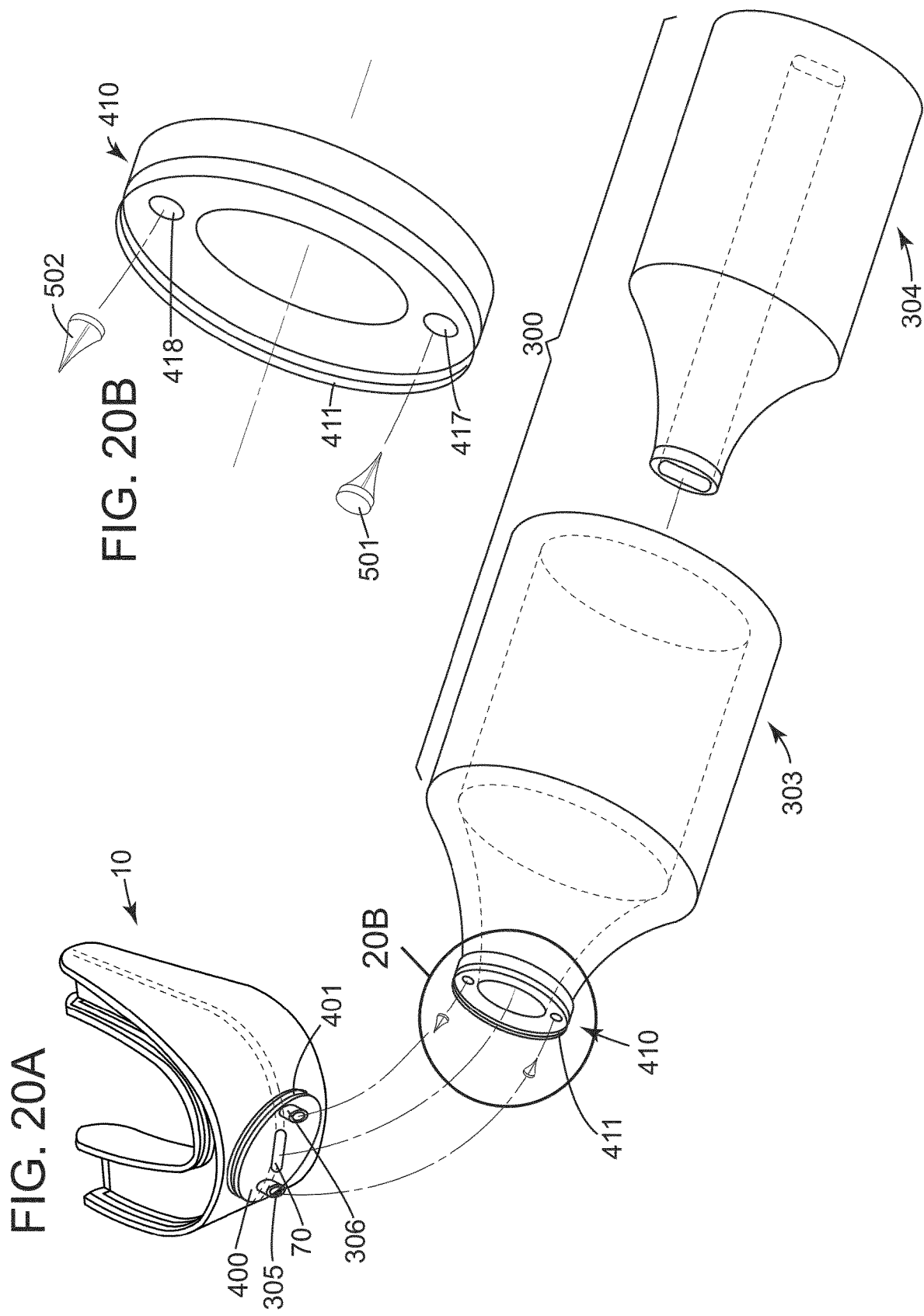

FIG. 19 is a top view of the mouth piece illustrating the plurality of bladders housing the salt water solution which flows from the salt water chamber 303 via one or more channels 305 and 306. The mouth piece and external chamber are kept in a freezer before use so that the water that is stored in the pure water chamber 304 is frozen. The pure water chamber 304 will provide a cooling effect for the salt water flowing through the bladders in the mouth piece as illustrated by the arrows in the drawing. In the illustrated embodiment, a series of cooling chambers (bladders) 181-184 are provided along the interior walls of the mouth piece 10. The distribution of the cooling medium between several connected chambers provides a malleable surface for contacting the gums of the patient without interfering with the breathing hole 70. The number and sizes of the discreet chambers can vary depending on the overall size of the mouth piece and the particular patient being treated. The series of bladders form a completely connected network. For example, bladder 189 is positioned at the rear surface of the mouth piece and connects bladder 181 to bladder 182. Similarly, bladder 190 is positioned at the rear surface of the mouth piece and connects bladder 183 to bladder 184. Preferably, each bladder is fixedly attached to the mouth piece with an appropriate adhesive or other means to prevent its dislodgement during use. In another embodiment, the chambers are removably attached and can be interchanged with various size bladders to control the amount and timing of cooling; or to adjust the fit of the mouth piece for the user's unique dental anatomy. For example, patients may have one or more teeth that are recessed or crooked from the adjacent teeth and a smaller or larger bladder can be fitted in this location of the mouth piece to accommodate for this discrepancy and therefore create more of a custom fit.

FIG. 20A is a front, top, and left side perspective exploded view of the mouth piece of FIG. 16, wherein the external chamber 300 is removed from the mouth piece 10. In one embodiment, the external chamber 300 includes a salt water chamber 303 having a cavity forming a distal opening that is configured and dimensioned to receive the pure water chamber 304 in a nested arrangement. Each of the salt water chamber 303 and pure water chamber 304 can include tapered proximal end portions. A flexible, insulation membrane (not shown) can surround the external chamber to provide insulation to the surrounding air, which is presumably a warmer temperature of about of 72 degrees F., when treating a patient in a clinical setting.

Because the external chamber 300 is removable from the mouth piece 10, the mouth piece can be manufactured in a variety of sizes to accommodate various patients, ranging from pediatric patients to adult men. However, the external chamber only needs to be manufactured in a limited number of sizes because it is able to connect to any size mouth piece. This allows a highly customizable fit for the elements that fit within the mouth, while minimizing unnecessary manufacturing and tooling costs for the external chamber. Furthermore, only the external chamber needs to be put into a refrigerator prior to use, thereby allowing a maximum number of external chambers to be stored per refrigerator. In addition, and especially for longer treatments, a second external chamber can be kept in the refrigerator and then swapped with the first external chamber originally attached to the mouth piece, and this can all be done while the mouth piece remains inside the patient's mouth, making this swap very easy to do.

Mating elements are dimensioned and configured to permit a proximal end of the first external chamber 303 to be removably attached to the front of the mouth piece 10. In one embodiment, the mating elements include tongue and groove mating surfaces 401 and 411 to permit a snap fit attachment. In another embodiment, the mating elements include threaded mating surfaces (not shown) to permit a removable screw fit attachment. This can also be accomplished by utilizing a separate threaded collar. In one embodiment, the mouth piece includes a cylindrical protrusion 400 having a side wall that includes grooves 401. One or more channels 305 and 306 can extend from the cylindrical protrusion 400 and are configured to align with one or more corresponding apertures 417 and 418 (see FIG. 20B) that provide conduit(s) into the salt water chamber 303.

FIG. 20B is a front and left side perspective exploded view of the proximal end of the external chamber showing a cylindrical member 410 and valves 501 and 502 for controlling the flow of the cooling medium. In one embodiment the valves 501 and 502 are duck bill valves, which include a flexible tunnel that is configured to open when pressure is applied by the flow of the cooling medium. The flexible tunnel can be conically-shaped as illustrated or can be other suitable shapes. The pressure can be applied by a user squeezing the outside of the salt water chamber 303, which is configured to remain pliable during use. Preferably, the valves are oriented to direct the fluid in a one-way flow pattern through the mouth piece to reduce turbulence and maximize the heat transfer and cooling effects inside the mouth by providing continuing circulation of the salt water to assist in maintaining the temperature. For example, valve 501 can direct flow in a distal direction and valve 502 can direct flow in a proximal direction.

Other types of valves can be utilized with the invention, including one-way type valves. In other embodiments, the valves can include handles that are adjustable by a user to open and close them. In other embodiments, the valves can include ball valves. The valves should be fixedly attached to the apertures 417 and 418. Alternatively, the valves can be positioned and fixedly attached to the channels 305 and 306 of the mouthpiece. In still another embodiment, valves can be included on both the apertures 417 and 48 and on the channels 305 and 306. In another embodiment, no valves are used and instead one or more flaps secured by adhesive or the like covers the conduits until a suitable pressure is applied which then opens or breaks the flap material to allow flow of the cooling medium. In another embodiment, nothing is used to seal the conduits and instead the external chamber 300 is maintained in an upright position so that gravity prevents any fluid from leaking out of the apertures 417 and 418. In another embodiment, one or more relief apertures are included with the device to allow entrapped air bubbles to escape from the otherwise closed loop system, should any such air bubbles exist.

Figure 21:
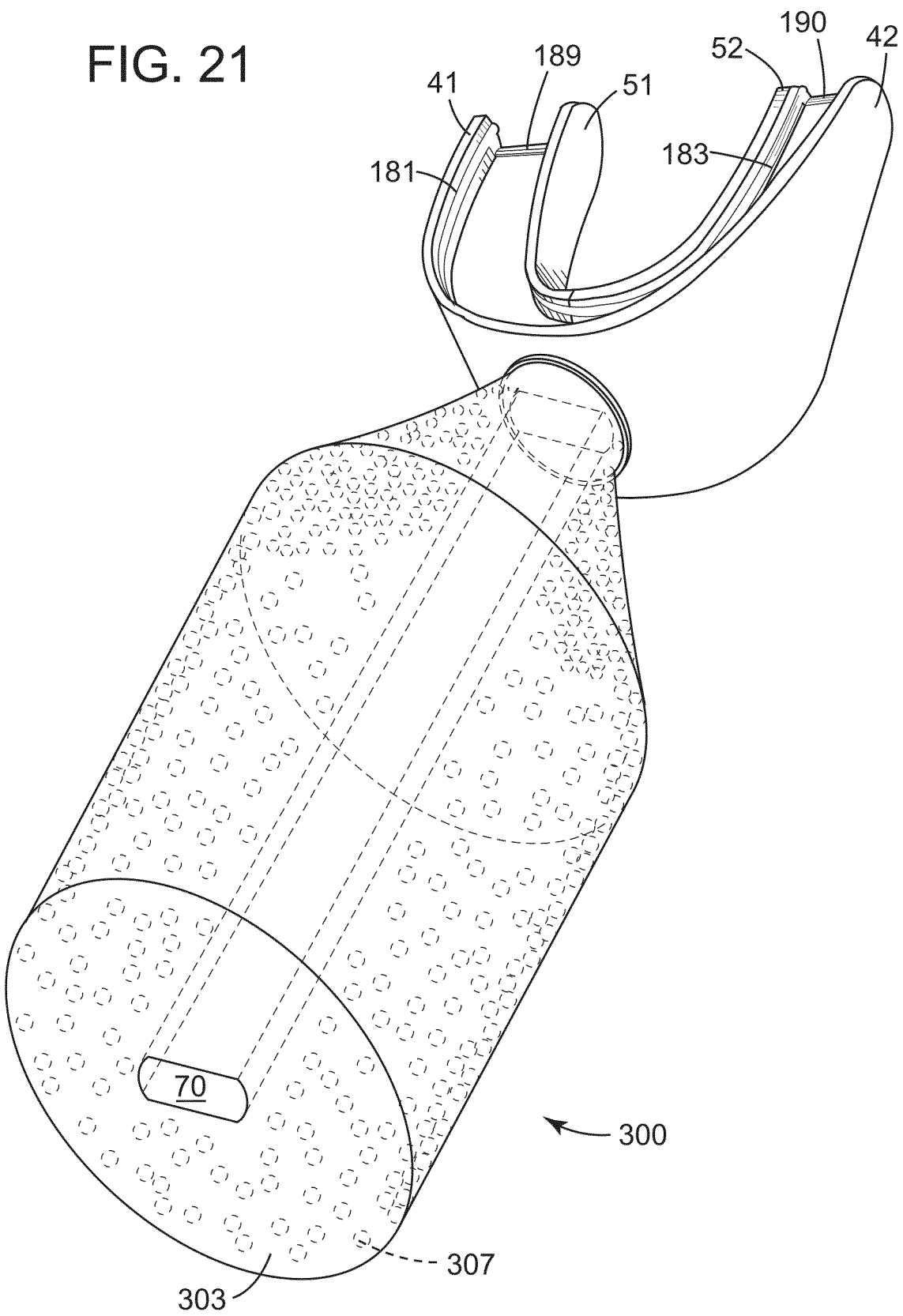
Figure 22:
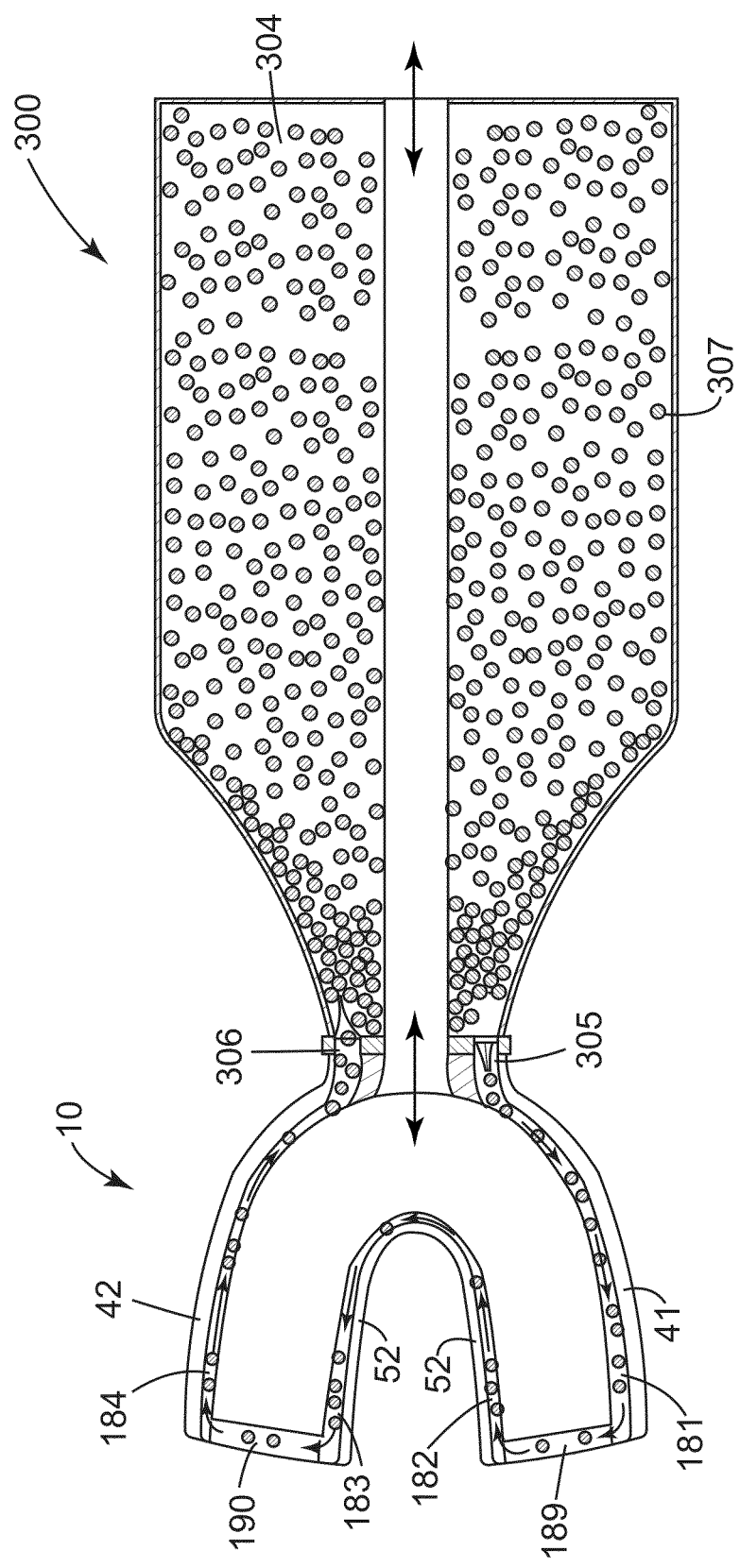

FIGS. 21-22 illustrate a sixth embodiment of the invention. FIG. 21 illustrates a front, top, and left perspective view of the mouth piece of FIG. 12, wherein the cooling medium bladders for the upper gums are shown and are connected to the external chamber 300, wherein the external chamber includes a salt water chamber 303 and a plurality of pure water capsules 307 that move freely inside the salt water chamber 303 and flow freely through the cooling medium bladders. The pure water capsules 307 can be spherically shaped or can be other shapes, including random amorphous shapes. Preferably, each pure water capsule 307 is uniformly sized to be of approximately similar volume.

FIG. 22 is a top view of the mouth piece of FIG. 21 illustrating a series of connected bladders for receiving both the salt water cooling medium and the pure water capsules 307 which flow freely throughout the top element and the bottom element. In one embodiment, the pure water capsules 307 are about 4 to 5 mm in diameter and the channels 305 and 306 are about 23 to 28 mm in diameter to permit the free flow of the pure water capsules throughout the mouthpiece 10. The water capsules 307 and channels 305 and 306 can be of any other suitable dimensions, as long as the water capsules are small enough to freely pass through the channels without becoming clogged.

Figure 23:
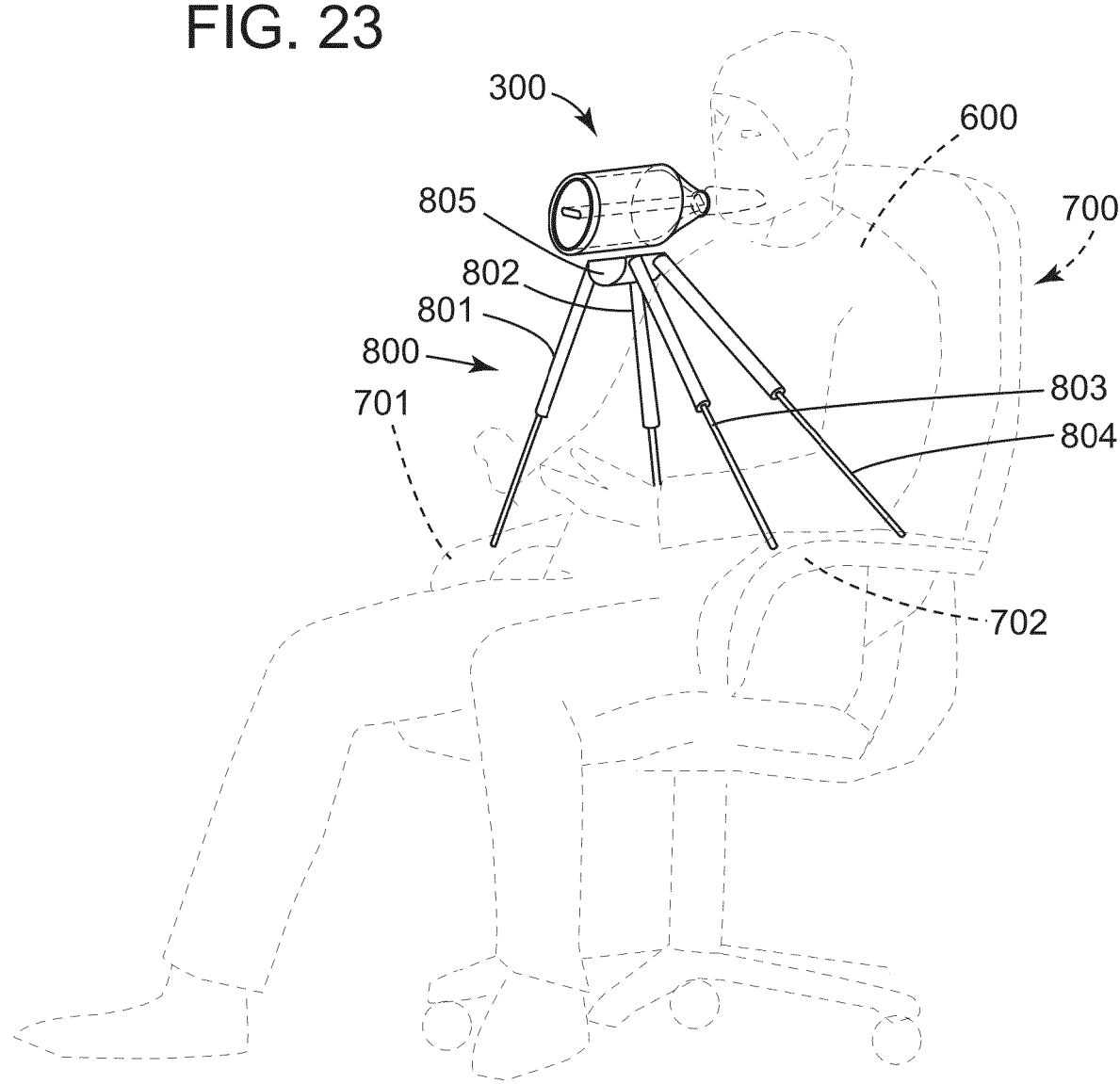
FIG. 23 illustrates a seventh embodiment of the invention, further comprising a support device including support legs and a sling.

FIG. 23 illustrates a seventh embodiment of the invention, further comprising an optional auxiliary support device 800 including support legs 801-804 and a sling 805. The auxiliary support device for the external chamber provides greater comfort in use and prevents muscle fatigue to the user. The support legs can be configured to telescope and adjust to accommodate various positions and provide sturdy support. For example, the support device 800 can be utilized to support the external chamber 300 by resting the support legs 801 and 802 on a right arm rest 701 and then resting support legs 803 and 804 on a left arm rest 702 of a chair 700 while a user 600 is seated. In another example (not shown), the support device 800 can be utilized to support the external chamber 300 by resting the support legs 801-804 on the chest of the user 600 while seated in a more reclined positioned.

Figure 24:
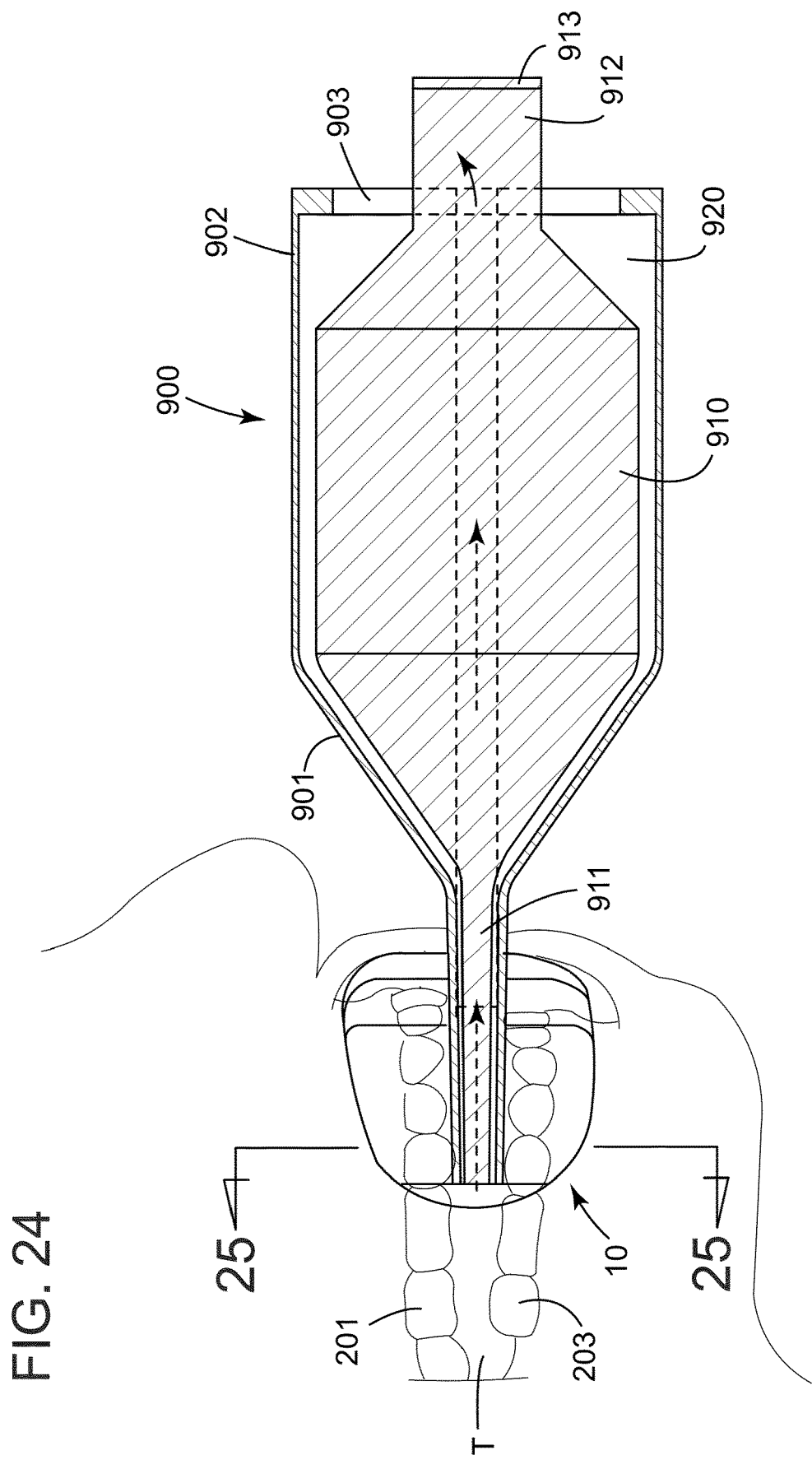

FIGS. 24-34 illustrate an eighth embodiment of the invention. FIG. 24 is an illustrational view of a mouth piece located within the mouth of a patient undergoing chemotherapy treatment, wherein an external chamber 900 extends from the front of the mouth piece.

The external chamber 900 preferably includes a pure water bladder 910 and a gap 920 is formed between the bladder 910 and external chamber 900 for holding salt water. An insulation layer (not shown) can be included to provide a barrier between the pure water bladder 910 and the surrounding salt water. In one embodiment, the bladder 910 is made from a material that is not permeable to salt, such as a latex based material. The bladder 910 stores a second solution having a freezing temperature above the freezing point temperature of the salt water to assist in cooling the salt water. In a preferred embodiment, the second solution that is stored inside the bladder 910 is pure water. In one embodiment, the external chamber 900 includes an outer insulation wall (not shown) that provides elasticity to allow a user to squeeze the contents and assist the flow of the cooling medium.

Although salt water and pure water are preferred because of their safety and ready availability, other materials which, like salt water, have a freezing point well below 0 degrees C. and pure water with a freezing point of 0 degrees C., other solutions in which the freezing point of one solution is close to 0 degrees C. and the other of which has a freezing point below 0 degrees C. can be substituted either for the salt water, pure water or both. In one embodiment, the salt water solution includes a mixture of salt in the range of 1% to 25% ratio. In one embodiment, the salt water solution includes a mixture of salt at a 10% ratio, which allows the solution to remain in liquid form down to about 17 degrees F. In one embodiment, the temperature of the mouth piece is in the range of 20 degrees to 25 degrees F. during treatment.

The mouth piece includes a top element 18 and a bottom element 19, which collectively provide total mouth coverage and cooling during chemotherapy treatment. The top element 18 is integral with or connected to the bottom element 19 to permit emplacement in the mouth as a one-piece unit. The top element 18 consists of a malleable material and is configured to rest adjacent at least major surfaces of the upper gums 211 and 212 and upper teeth 201 and 202 of a patient's mouth in a close-fitting relationship. The bottom element 19 consists of a malleable material and is configured to rest adjacent at least major surfaces of the lower gums 213 and 214 and lower teeth 203 and 204 of a patient's mouth in a close-fitting relationship.

Figure 25:
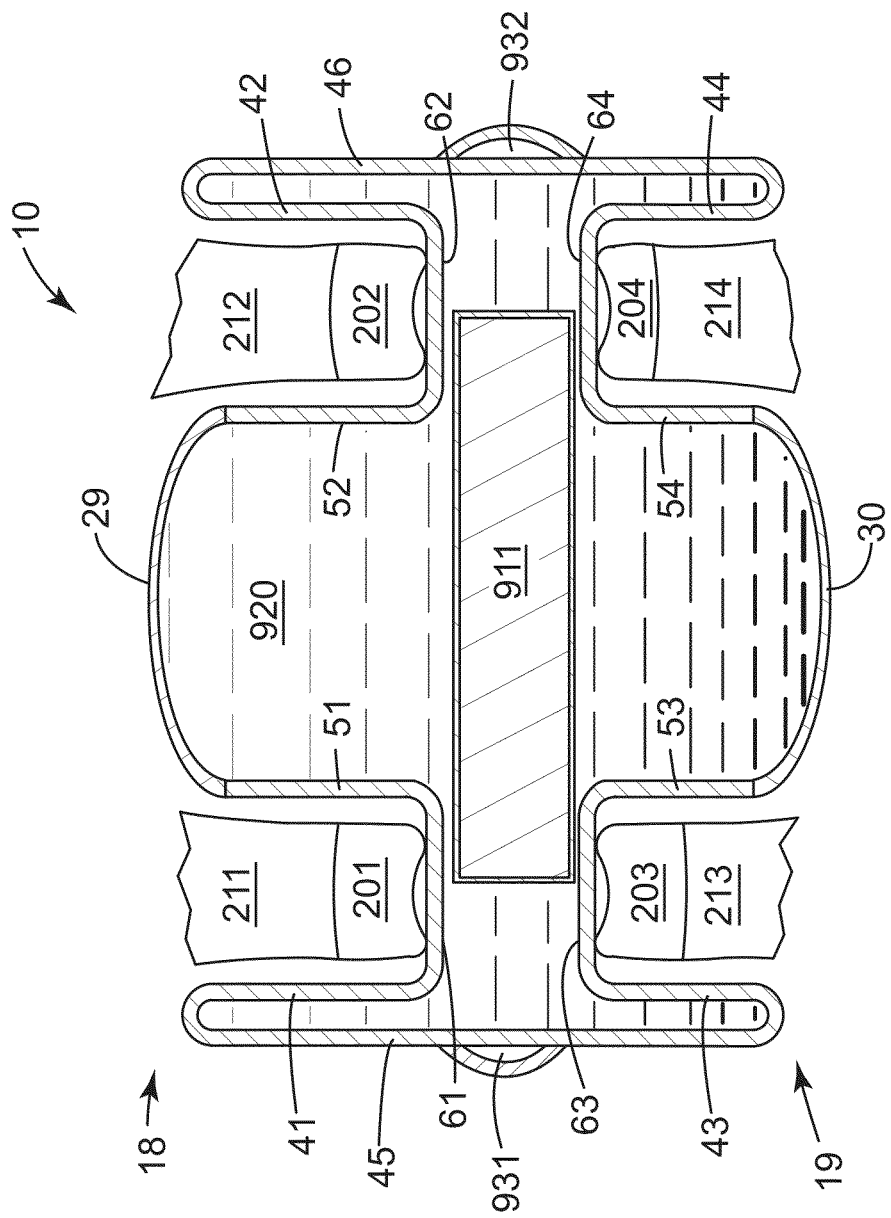

FIG. 25 is a cross-sectional view of a mouth piece taken in the direction of line 25-25 of FIG. 24, in accordance with the eighth embodiment. The patient's right upper teeth 201 and right upper gums 211 engage the top right walls 41, 51 and 61, which collectively form a U-shaped cavity. The mouth piece includes is preferably formed from a single layer of material that is bent and folded at certain predetermined locations to form a single, continuous internal cavity 920 that surrounds the proximal end 911 of the pure water bladder 910. In particular, the wall of the mouth piece is bent to form a right outer wall 45 that holds the mouth piece together and forms areas of the cavity that reside adjacent the patient's right teeth and gums (both upper and lower). Similarly, the wall of the mouth piece is bent to form a left outer wall 46 that joins the mouth piece and forms areas of the cavity that reside adjacent the patient's left teeth and gums (both upper and lower). It should be understood that the mouth piece is sized appropriately, such that the patient's teeth and gums fit inside the U-shaped cavities in a close-fitting relationship. Therefore, although FIG. 25 illustrates a space between the outer surfaces of the patient's teeth and gums and the walls of the U-shaped cavities, in other embodiments (not shown), there is no such spacing (or minimal spacing) and the patient's teeth and gums rest directly against the walls of the U-shaped cavities. Similarly, the other remaining quadrants of the patient's mouth are treated in the same manner as described above and therefore do not require further discussion.

The proximal end 911 of the pure water bladder 910 can be rectangular in cross-section. In other embodiments, the proximal end 911 of the pure water bladder 910 can be oval in cross-section or can have other cross-section shapes, including amorphous shapes. The proximal end 911 of the pure water bladder 910 is configured and dimensioned to fit between the right biting surface walls 61 and 63 and to fit between the left biting surface walls 62 and 64. In addition, the proximal end 911 of the pure water bladder 910 is configured and dimensioned to fit between right outer wall 45 and left outer wall 46. Furthermore, a sufficient gap or space should be permitted fully surrounding the proximal end 911 of the pure water bladder 910 to permit the surrounding salt water to freely flow over and in-between all surfaces of the mouth piece to maximize the cooling effect and to attempt to maintain substantially uniform temperatures inside the mouth.

Figure 26:
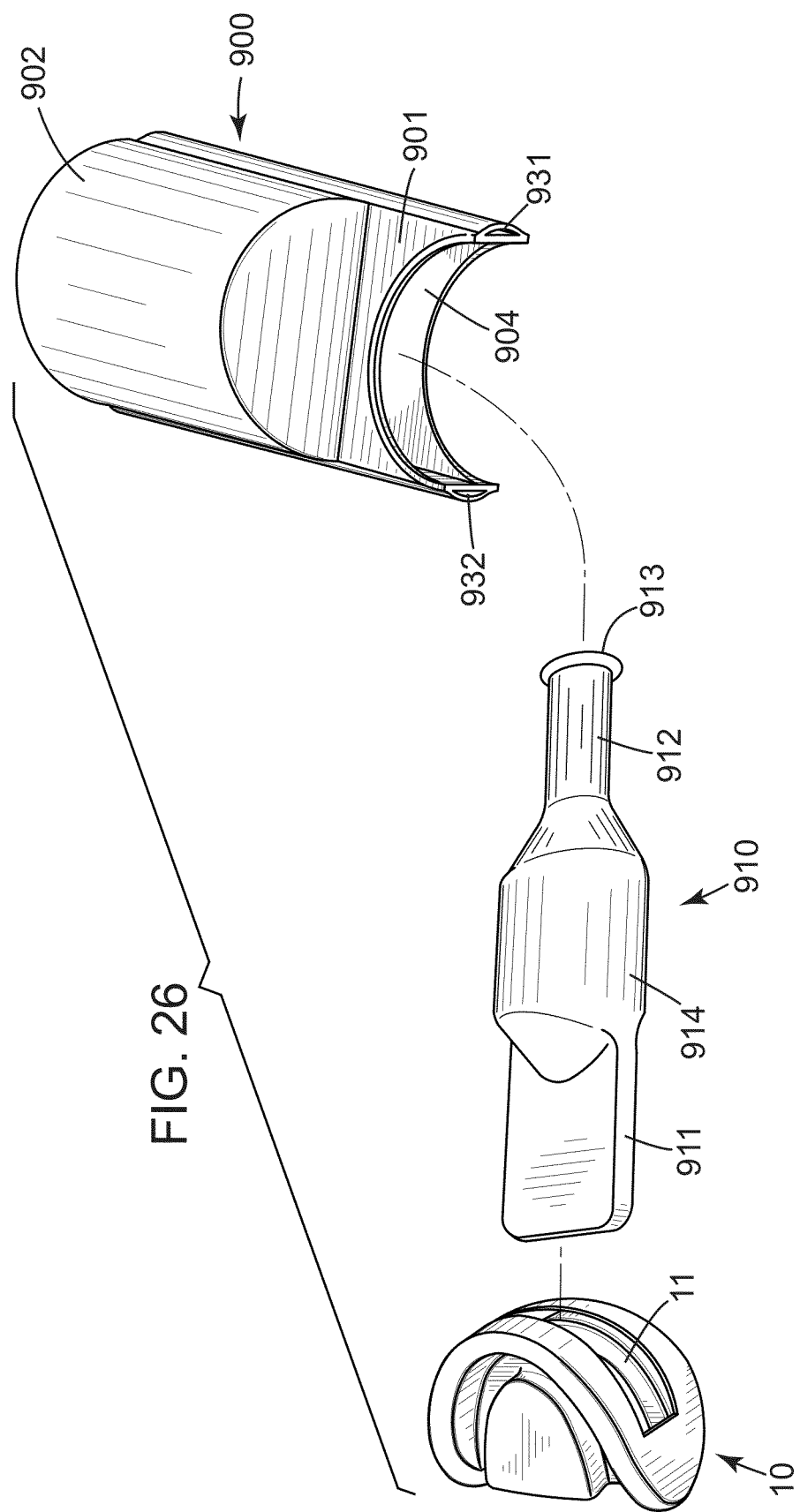

FIG. 26 is a right side perspective exploded view of the mouth piece of FIG. 24, wherein the bladder 910 is shown positioned ready for insertion between the mouth piece 10 and the external chamber 900. Two opposing breathing tubes 931 and 932 are positioned in lateral locations and extend longitudinally along the outside surface of the external chamber 900 that permit a patient to breathe through the mouth when the mouth piece 10 is emplaced within the mouth in the operative close-fitting relationship. Although the breathing tubes 931 and 932 are illustrated as two separate breathing tubes, the quantity of breathing tubes is not considered limiting. In other embodiments, one or more breathing tubes can be positioned along the top and/or bottom edges of the external chamber 900 or positioned along any other axis. For all embodiments of the invention, the breathing tubes and/or its apertures can be round, slotted, oval, rectangular, or any other shape. The interior wall of the breathing tubes can be made from a rigid or semi-rigid material, such as plastic, hard rubber, and the like, in order to maintain its shape under the weight of the external chamber 900 without crimping.

As illustrated, the mouth piece 10 includes a frontal opening 11 that is configured and dimensioned to permit the insertion of the proximal end 911 of the pure water bladder 910. In addition, the frontal opening 11 is configured and dimensioned to correspond to the size of the proximal opening 904 that is formed in the proximal end 901 of the external chamber 900. In the embodiment illustrated in FIG. 26, the mouth piece 10 and the external chamber 900 are separate parts. Although not shown, the distal end 902 of the external chamber 900 includes a distal wall that seals the external chamber closed. In this embodiment, the bladder 910 is filled with pure water and then the opening 913 is sealed. Then, the bladder is inserted between the mouth piece 10 and the external chamber 900. Next, the mouth piece 10 is sealed to the external chamber to form a water-tight seal, by using an adhesive sealant or other type of bonding agent. Finally, a syringe is used to pump salt water inside the external chamber 900 into the gap surrounding the bladder 910.

Figure 27:
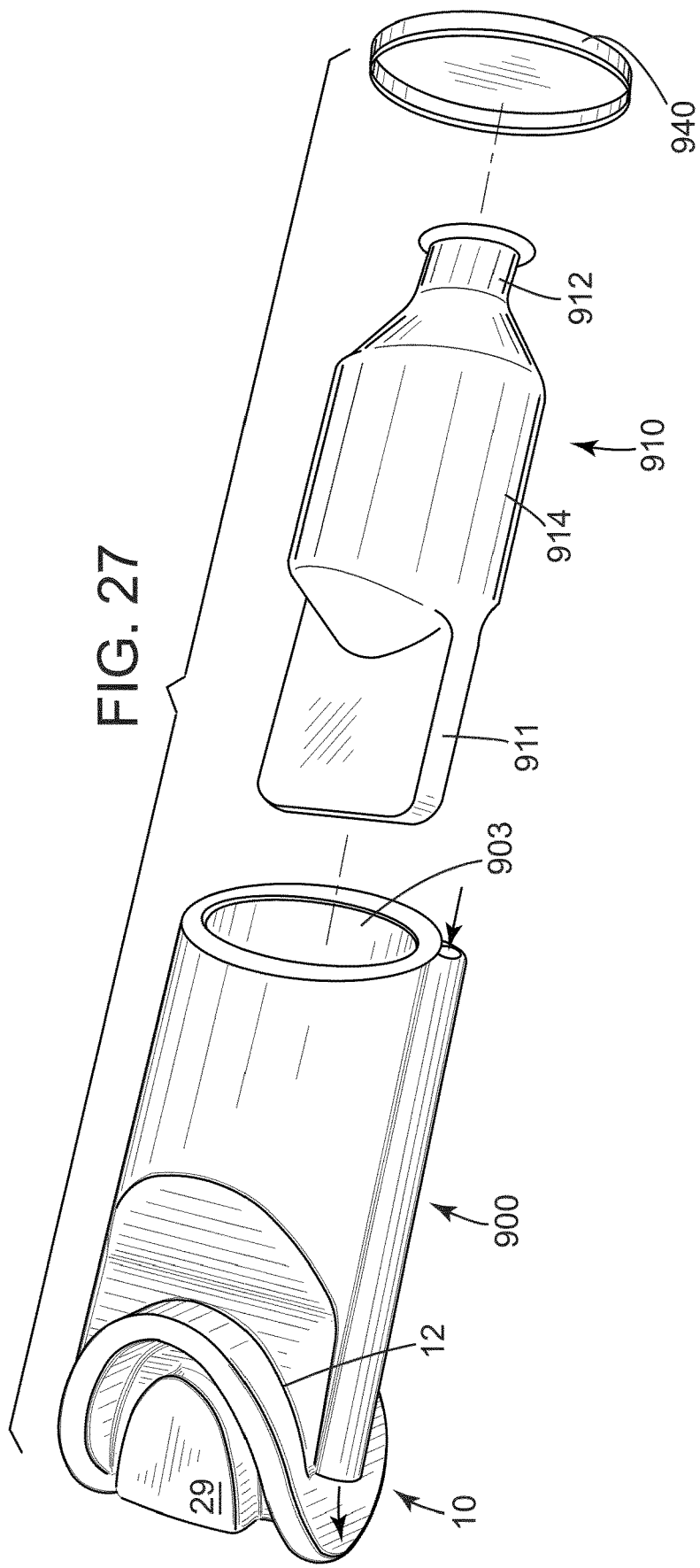

FIG. 27 is a right side perspective exploded view of the mouth piece of FIG. 24, wherein the bladder 910 is shown positioned ready for insertion between the external chamber 900 and a cap 940. The mouth piece and external chamber are kept in a freezer before use so that the water that is stored in the pure water bladder 910 is frozen. The pure water bladder 910 will provide a cooling effect for the salt water flowing through the external chamber 900 and the mouth piece 10. In the illustrated embodiment, the mouth piece 10 and the external chamber 900 are integrally formed as a one-piece unit, for example by manufacturing from a single mold. In this embodiment, once the bladder 910 is filled with pure water, it is inserted into the external chamber 900, and then a cap 940 is used to seal the external chamber as a water-tight seal. The cap can be sealed through a screw-fit arrangement, a snap-fit arrangement, a heat activated adhesive, and/or any other type of bonding agent or adhesive. The distribution of the cooling medium between the external chamber 900 and the mouth piece 10 provides a cooling effect to the patient's mouth without interfering with the breathing holes positioned along the outside of the external chamber 900.

In a preferred embodiment, the bladder 910 includes a proximal end 911 and a distal end 912 and a central portion 914. The proximal end 911 and the central portion 914 form an outer surface profile that corresponds to the inner surface profile of the external chamber 900 to permit emplacement in a nest arrangement. Preferably, the bladder 910 is freely placed inside the external chamber 900. This allows the bladder 910 to expand during freezing, and contract should the ice begin to melt. However, in other embodiments, the bladder 910 can be attached to the inside surface of the external chamber 900 at one or more locations to maintain its relative position within the external chamber.

Figure 28:
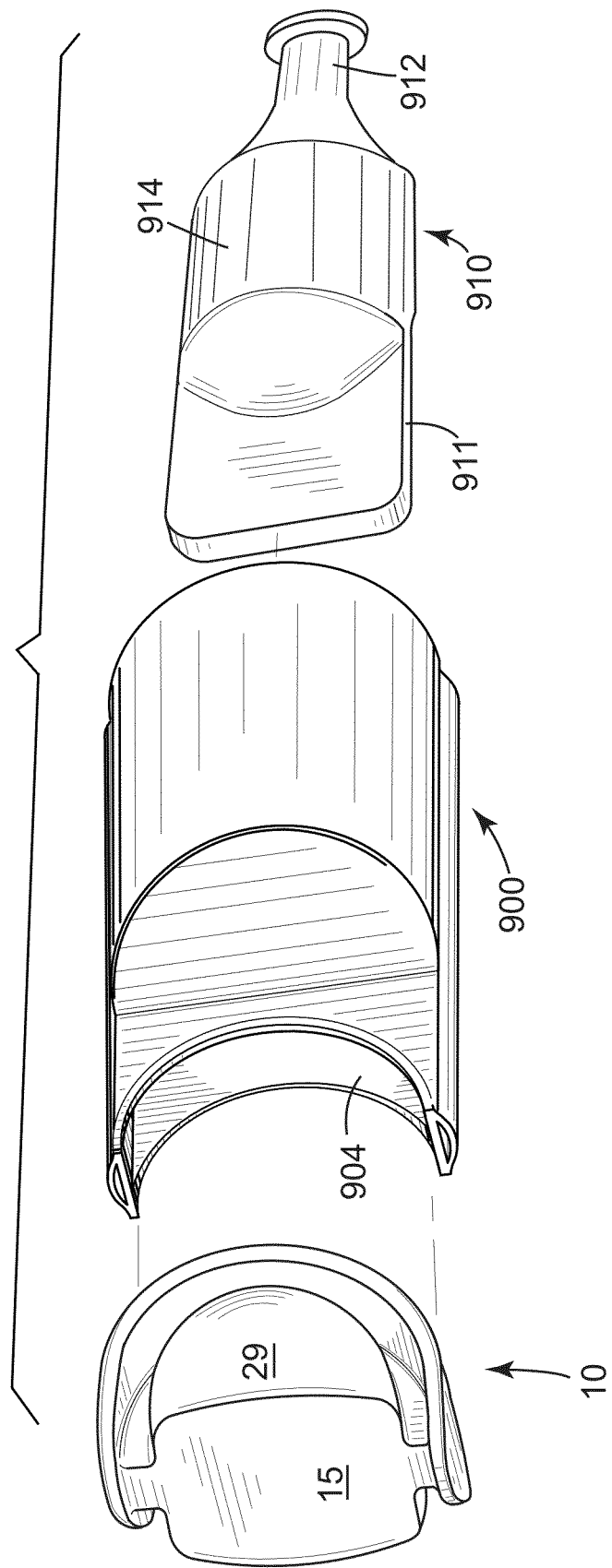

FIG. 28 is a right side perspective exploded view of the mouth piece of FIG. 24, showing the proximal wall 15 of the mouthpiece 10 that connects the top element and the bottom element. Furthermore, an upper wall 29 and corresponding lower wall 30 (not shown) act together with the proximal wall 15 to both form the outer surfaces of the cavity of the mouth piece while also providing a general framework for supporting the mouth piece and its liquid contents. In one embodiment, the material used for these surfaces in particular of the mouth piece can be somewhat more rigid than other surfaces to maintain the desired shape of the mouth piece during use. In all embodiments of the invention, the material should be durable enough to maintain a water-tight seal during treatment of a patient and be able to withstand any forces applied should the patient bite down on the mouth piece during use. For example, a metallic mesh material can be embedded within the external surfaces to prevent puncturing or other possible damage that could cause a leak to occur. In any event, should a leak occur, there is no harm to the patient because the contents are non-toxic and preferably include water, salt, and other harmless substances.

In all embodiments of the invention, the mouth piece can be manufactured in a variety of sizes to accommodate various patients, ranging from pediatric patients to adult men. However, the external chamber only needs to be manufactured in a limited number of sizes.

Figure 29:
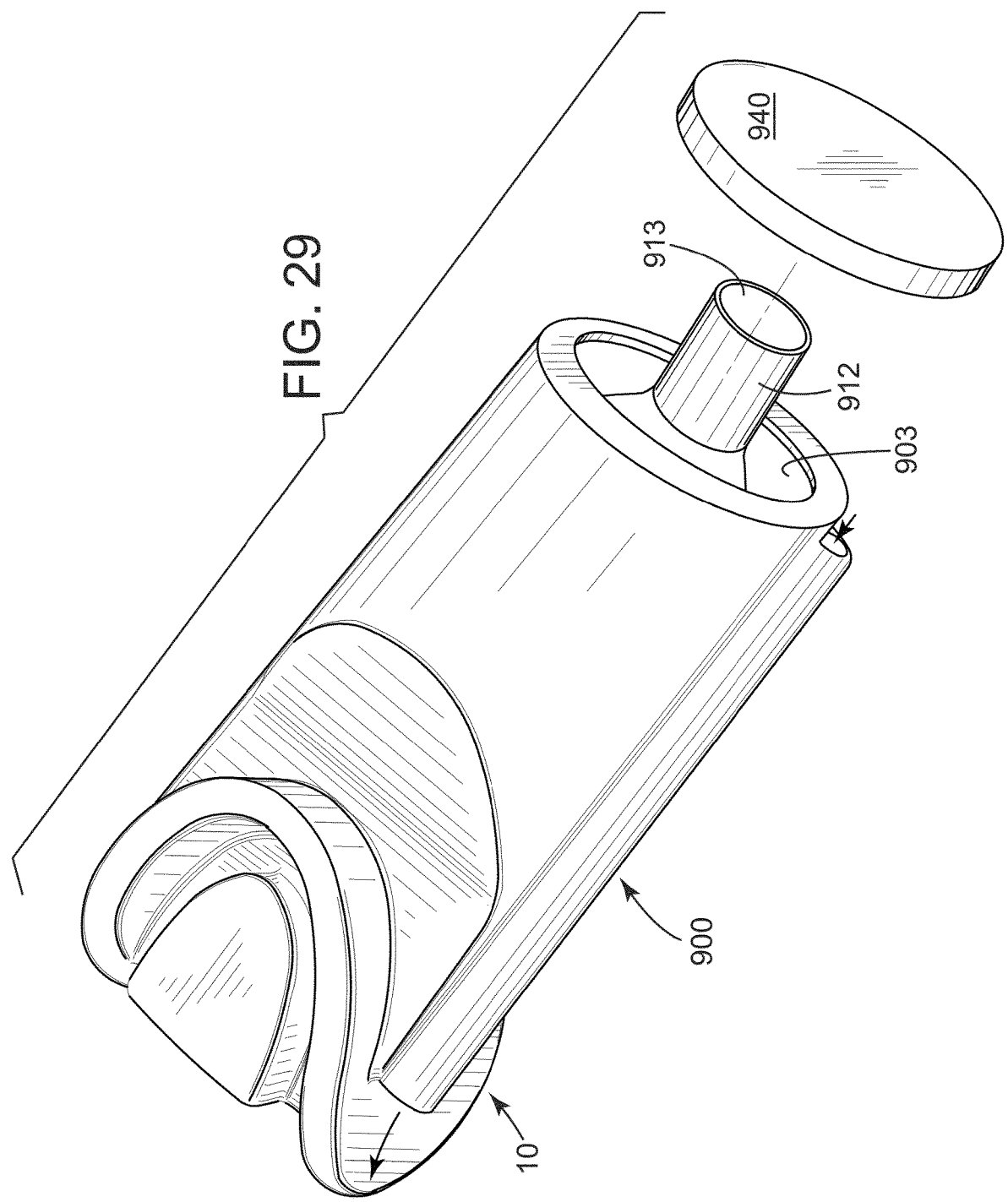

FIG. 29 is a right side perspective exploded view of the mouth piece of FIG. 24, showing the bladder inserted inside the external chamber 900. In one embodiment, the distal end 912 of the bladder extends beyond the length of the external chamber 900. The opening 913 of the pure water bladder 910 is sealed before placing the cap 940 over the external chamber 900. In one embodiment, a stopper (not shown) can be placed inside the opening 913 of the bladder to create a water tight seal.

Figure 30:
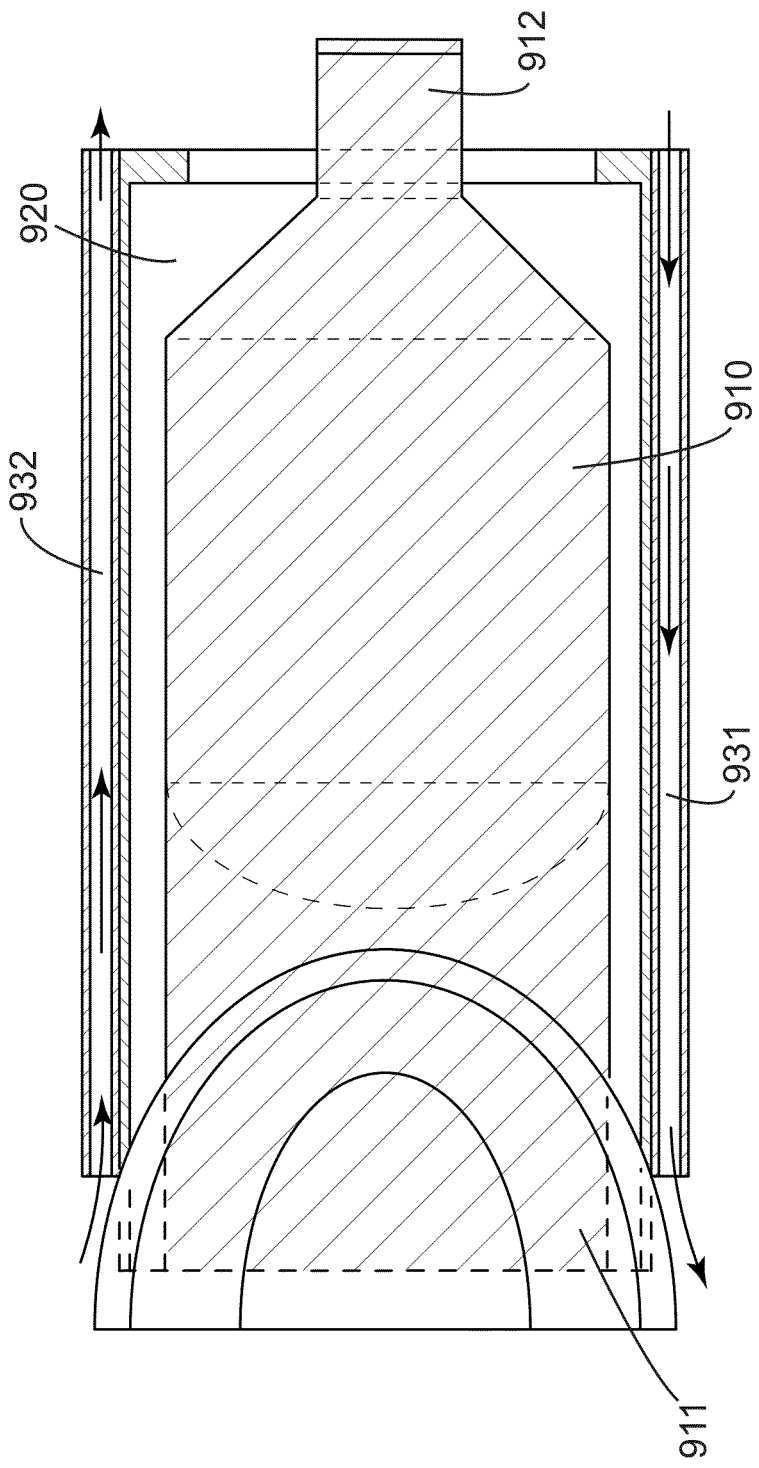

FIG. 30 is a top view of the mouth piece of FIG. 24 illustrating the bladder 910 for receiving the cooling medium which flows throughout the top element and the bottom element. As discussed above, the proximal end 911 of the bladder 910 preferably extends, at least partially, between the upper and lower teeth of the patient to maximize the cooling effect during treatment. In one embodiment, the gap 920 that surrounds the bladder 910 extends substantially all the way around the bladder 910, including the proximal most end of the mouth piece.

In the embodiment described in FIGS. 24-30, a patient may only need to retain the mouth piece inside the mouth for 30 minutes to achieve the desired cooling effect during treatment. In one embodiment, the mouth piece achieves a temperature inside the mouth between 50 degrees and 60 degrees F.

In another embodiment, the external chamber can further include one or more heat sensitive indicia that change color to indicate when the temperature has reached the desired starting temperature and ending temperature for use during treatment. For example, the indicia can show a green color when a predetermined temperature has been reached during storage that is considered sufficient to be inserted inside the mouth. Likewise, the indicia can show a yellow color when a predetermined temperature has been reached during use such that the effectiveness of the mouth piece has subsided and it is time to remove the mouth piece from the mouth, thereby ending the use and possible replacement with another secondary mouth piece that is ready and waiting to be placed inside the mouth. In another embodiment, the indicia can show a red color if the temperature of the device has reached a predetermined temperature that is considered too cold for placement inside the mouth of the patient, which could cause discomfort or possible harm to the patient. Any other color coding can be utilized or other types of indicia that is reactive to temperature changes.

In one embodiment of the invention, the device is shipped to the customer in a ready-to-use assembly, such that the bladder is not removable from the external bladder, and both the bladder and external chamber have been pre-filled with the first solution and the second solution. In one embodiment, the device is intended to be used as a one-time use only device.

Figure 31:
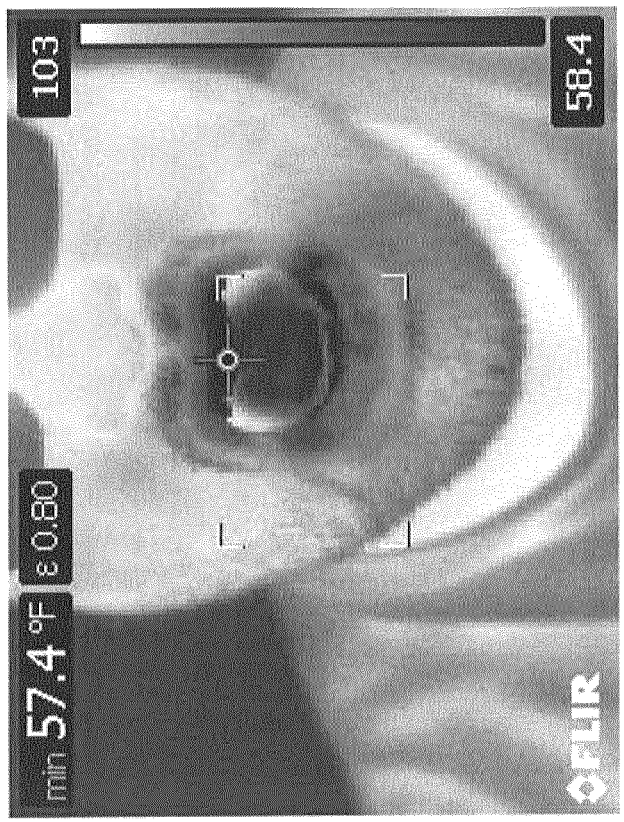
Figure 32:
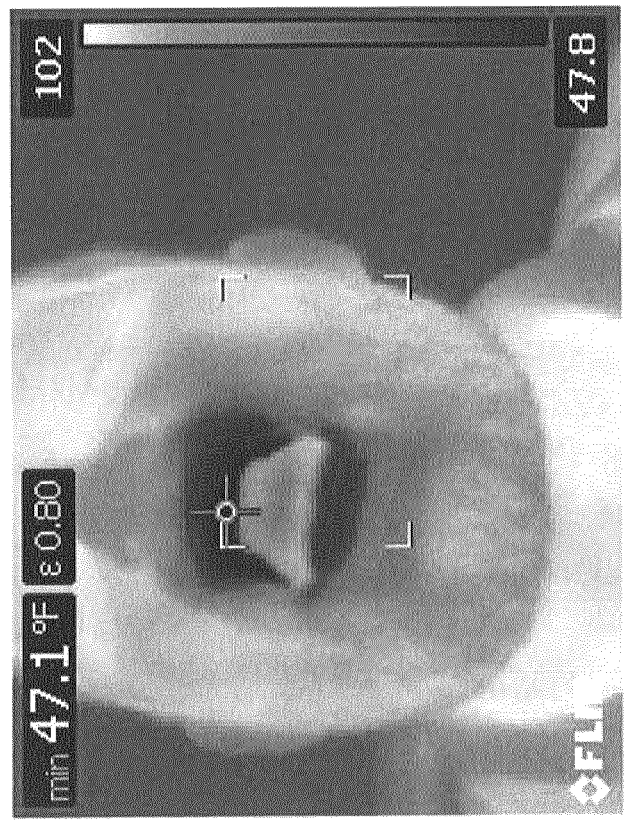

FIGS. 31-32 are intra oral infrared temperature images showing the cooling effects of the mouth piece on a first test subject.

Figure 33:
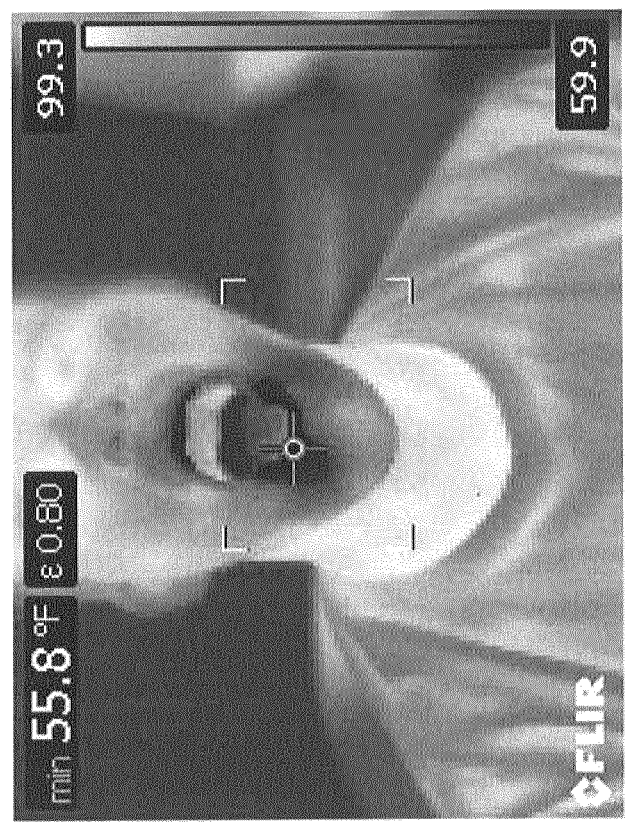
Figure 34:
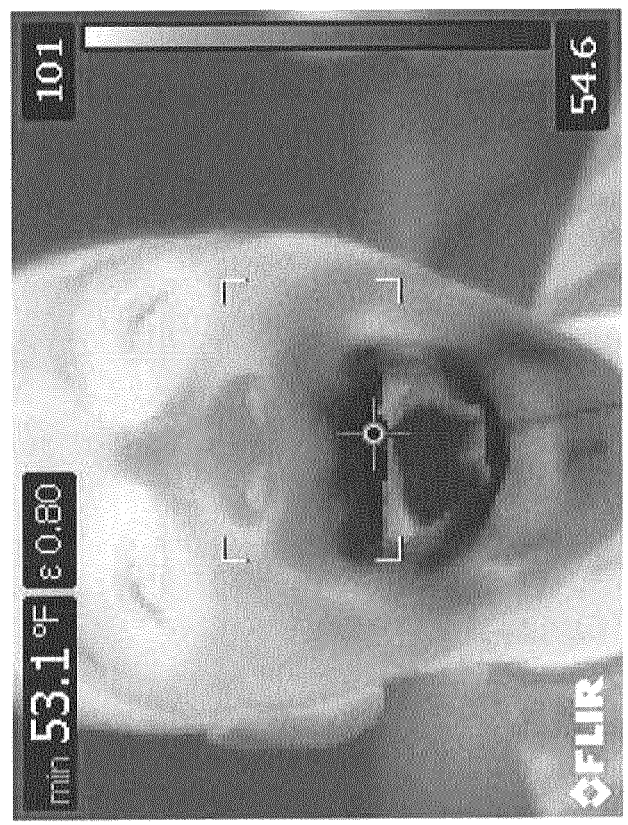

FIGS. 33-34 are intra oral infrared temperature images showing the cooling effects of the mouth piece on a second test subject.

In another embodiment (not shown), an electric cooling device can be utilized that is battery powered or is directly plugged into an electrical wall socket, wherein the cooling device is adapted to cool the external chamber. The cooling device includes a power switch and can be used to supplement the cooling of the cooling medium or as the primary means for cooling the cooling medium.

The foregoing description of the preferred embodiment of the invention has been presented to illustrate the principles of the invention and not to limit the invention to the particular embodiment illustrated. It is intended that the scope of the invention be defined by all of the embodiments encompassed within the following claims, and their equivalents.

The invention claimed is:

1. A hand-held therapeutic oral device for cooling of oral tissue of a user comprising:
an elongated casing having a proximal end and a distal end, the proximal end formed as a mouthpiece configured for insertion into a user's mouth, the mouthpiece including;
a malleable top element configured to rest adjacent at least major surfaces of the upper gums and teeth of the user's mouth in a close-fitting relationship,
a malleable bottom element configured to rest adjacent at least major surfaces of the lower gums and teeth of a patient's mouth in a close-fitting relationship,
wherein the top element is integral with or connected to the bottom element to permit emplacement in the mouth as a one-piece unit;
wherein the distal end of the casing forms a first bladder that stores a first coolant having a first freezing temperature, the first coolant being in fluid communication with the mouthpiece;
a second bladder positioned within the first coolant of the first bladder, the second bladder storing a second coolant having a second freezing temperature above the first freezing point temperature of the first coolant to assist in cooling the first coolant;
wherein the top element and the bottom element contain a portion of the first coolant for cooling the oral tissue within the user's mouth; and
at least one breathing tube extending in a longitudinal direction from the proximal end towards the distal end and positioned along an exterior surface of the casing of the hand-held oral device, the at least one breathing tube configured to permit the user to breathe through the at least one breathing tube when the mouth piece is emplaced within the mouth of the user.

2. The hand-held therapeutic oral device according to claim 1, in which the first coolant is salt water.

3. The hand-held therapeutic oral device according to claim 1, in which the second coolant is water.

4. The hand-held therapeutic oral device according to claim 1, wherein the second bladder includes a proximal end, a central portion, and a distal end, wherein the second bladder is dimensioned and configured such that the proximal end is positioned at least partly between the top element and the bottom element.

5. The hand-held therapeutic oral device according to claim 4, in which the proximal end of the second bladder has a rectangular cross-section profile.

6. The hand-held therapeutic oral device according to claim 4, in which the central portion of the second bladder has a circular cross-section profile.

7. The hand-held therapeutic oral device according to claim 1, wherein the distal end of the casing has a circular cross-section profile.

8. The hand-held therapeutic oral device according to claim 1, wherein the distal end of the casing includes a distal wall that seals the first chamber closed.

9. The hand-held therapeutic oral device according to claim 1, wherein the distal end of the casing includes an opening that is configured and dimensioned to receive the second bladder.

10. The hand-held therapeutic oral device according to claim 9, further comprising a cap that is dimensioned and configured to seal the opening.

11. The hand-held therapeutic oral device according to claim 1, in which the casing is malleable to provide elasticity to allow a user to squeeze the contents and assist the flow of the cooling medium.

12. The hand-held therapeutic oral device according to claim 1, further comprising a proximal wall that connects the top element to the bottom element.

13. The hand-held therapeutic oral device according to claim 1, wherein the top element, the bottom element, and the first bladder are integrally formed as a one-piece unit.

14. The hand-held therapeutic oral device according to claim 1, wherein the first bladder is a separate part which is bonded to the top element and the bottom element during manufacturing to create a water tight seal.

15. The hand-held therapeutic oral device according to claim 1, wherein the first bladder is configured and dimensioned to receive the second bladder in a nested arrangement.

16. The hand-held therapeutic oral device according to claim 15, wherein each of the first bladder and the second bladder include tapered proximal end portions.

17. The hand-held therapeutic oral device according to claim 1, wherein the at least one breathing tube includes two breathing tubes, each of which extending on opposing lateral sides of the casing of the hand-held oral device.

18. The hand-held therapeutic oral device mouth piece of claim 1, wherein the first freezing temperature of the first coolant is below 0 degrees Celsius.

19. The hand-held therapeutic oral device mouth piece of claim 1, wherein the distal end of the casing is configured and dimensioned to enable the user to guide the mouthpiece of the hand-held oral device in and out of the user's mouth.

* * * * *